(12) United States Patent
Reimels

(10) Patent No.: US 11,134,935 B2
(45) Date of Patent: Oct. 5, 2021

(54) SOFT TISSUE RETRACTOR

(71) Applicant: Alphatec Spine, Inc., Carlsbad, CA (US)

(72) Inventor: William Reimels, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 15/619,896

(22) Filed: Jun. 12, 2017

(65) Prior Publication Data

US 2017/0273678 A1 Sep. 28, 2017

Related U.S. Application Data

(62) Division of application No. 14/425,535, filed on Mar. 3, 2015, now Pat. No. 9,693,762.

(60) Provisional application No. 61/946,986, filed on Mar. 3, 2014.

(51) Int. Cl.
*A61B 17/02* (2006.01)

(52) U.S. Cl.
CPC ............... *A61B 17/0206* (2013.01)

(58) Field of Classification Search
CPC .......................................... A61B 17/02–0293
See application file for complete search history.

(56) References Cited

U.S. PATENT DOCUMENTS

| 817,973 | A | | 4/1906 | Hausmann | |
|---|---|---|---|---|---|
| 3,680,546 | A | | 8/1972 | Asrican | |
| 3,749,088 | A | * | 7/1973 | Kohlmann | A61B 17/0293 403/107 |
| 4,130,113 | A | | 12/1978 | Graham | |
| 4,616,635 | A | * | 10/1986 | Caspar | A61B 17/02 600/215 |
| 5,183,032 | A | | 2/1993 | Villalta et al. | |
| 5,375,481 | A | * | 12/1994 | Cabrera | A61B 17/0293 248/316.4 |
| 5,520,610 | A | | 5/1996 | Giglio et al. | |
| 5,728,046 | A | | 3/1998 | Mayer et al. | |

(Continued)

FOREIGN PATENT DOCUMENTS

DE 202009009503 U1 9/2009
FR 542744 A 8/1922

(Continued)

OTHER PUBLICATIONS

International Search Report and Written Opinion for PCT/US2015/018270, dated Mar. 2, 2015.

(Continued)

*Primary Examiner* — Eduardo C Robert
*Assistant Examiner* — Steven J Cotroneo
(74) *Attorney, Agent, or Firm* — Robert Winn

(57) ABSTRACT

A tissue retractor device within the scope of the present invention generally includes a frame, an actuating mechanism, and a plurality of blades. The actuating mechanism generally includes at least one cam that encourages automatic toe-out of the blades. The tissue retractor eliminates the need for bulky secondary blade mechanisms to prevent undesired blade deformation at the surgical site. The toe-out motion occurs simultaneously along with the opening of the blades. The present invention further provides for depth adjustment of the blades by means of an adjustable screw assembly.

19 Claims, 20 Drawing Sheets

(56) References Cited

U.S. PATENT DOCUMENTS

| | | | |
|---|---|---|---|
| 5,931,777 A | 8/1999 | Sava | |
| 5,944,658 A * | 8/1999 | Koros | A61B 17/0206 600/231 |
| 6,074,343 A | 6/2000 | Nathanson et al. | |
| 6,139,493 A * | 10/2000 | Koros | A61B 17/0206 600/213 |
| 6,416,467 B1 * | 7/2002 | McMillin | A61B 1/32 600/220 |
| 6,468,207 B1 | 10/2002 | Fowler, Jr. | |
| 6,712,795 B1 * | 3/2004 | Cohen | A61B 17/0206 604/233 |
| 6,945,933 B2 | 9/2005 | Branch et al. | |
| 7,195,592 B2 | 3/2007 | Ravikumar et al. | |
| 7,207,949 B2 | 4/2007 | Miles et al. | |
| 7,582,058 B1 | 9/2009 | Miles et al. | |
| 7,691,057 B2 | 4/2010 | Miles et al. | |
| 7,780,594 B2 | 8/2010 | Hutton | |
| 7,785,253 B1 | 8/2010 | Arambula et al. | |
| 7,819,801 B2 | 10/2010 | Miles et al. | |
| 7,905,840 B2 | 3/2011 | Pimenta et al. | |
| 8,016,767 B2 | 9/2011 | Miles et al. | |
| 8,038,611 B2 | 10/2011 | Raymond et al. | |
| 8,137,284 B2 | 3/2012 | Miles et al. | |
| 8,882,661 B2 | 11/2014 | Hutton et al. | |
| 8,974,381 B1 * | 3/2015 | Lovell | A61B 17/0206 600/215 |
| 2003/0191372 A1 | 10/2003 | Dobrovolny | |
| 2004/0002629 A1 * | 1/2004 | Branch | A61B 17/0206 600/210 |
| 2005/0165281 A1 | 7/2005 | Ravikumar et al. | |
| 2006/0004261 A1 | 1/2006 | Douglas | |
| 2006/0084844 A1 | 4/2006 | Nehls | |
| 2006/0224044 A1 | 10/2006 | Marchek et al. | |
| 2007/0156024 A1 * | 7/2007 | Frasier | A61B 17/02 600/219 |
| 2007/0156026 A1 * | 7/2007 | Frasier | A61B 17/02 600/224 |
| 2007/0208227 A1 * | 9/2007 | Smith | A61B 1/313 600/219 |
| 2007/0208228 A1 * | 9/2007 | Pavento | A61B 17/0293 600/233 |
| 2008/0114208 A1 * | 5/2008 | Hutton | A61B 17/0206 600/201 |
| 2008/0300465 A1 * | 12/2008 | Feigenwinter | A61B 17/0293 600/201 |
| 2009/0093684 A1 | 4/2009 | Schorer | |
| 2009/0182203 A1 | 7/2009 | Hartnick et al. | |
| 2012/0046527 A1 | 2/2012 | Cianfrani et al. | |
| 2013/0190575 A1 * | 7/2013 | Mast | A61B 17/7079 600/215 |
| 2014/0005484 A1 | 1/2014 | Charles | |
| 2015/0351738 A1 | 12/2015 | Perrow | |
| 2016/0074029 A1 | 3/2016 | O'Connell et al. | |

FOREIGN PATENT DOCUMENTS

| | | |
|---|---|---|
| WO | 2001003586 | 1/2001 |
| WO | 2001028431 | 4/2001 |

OTHER PUBLICATIONS

Extended European Search Report for EP15758234, dated Oct. 16, 2017.

* cited by examiner

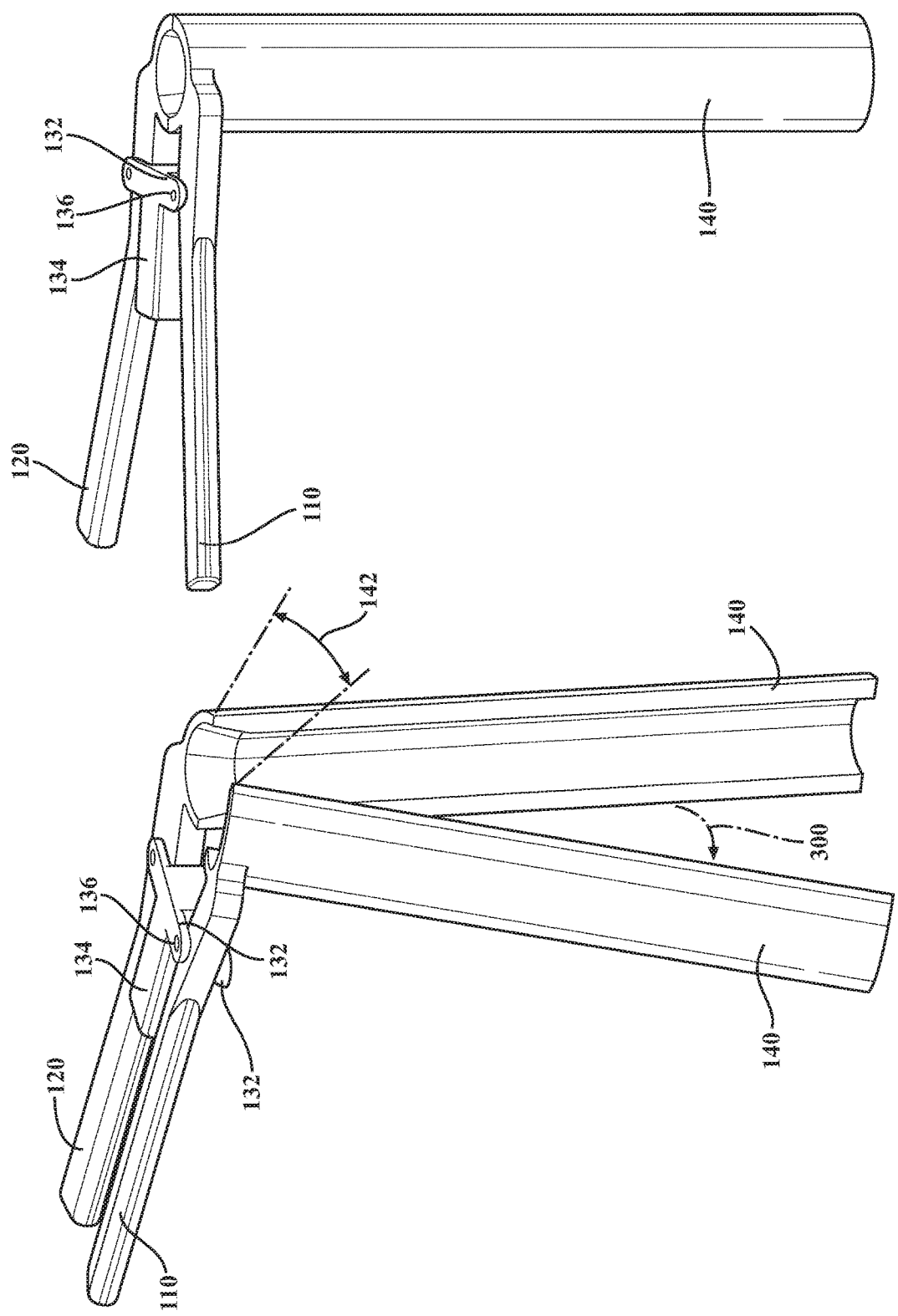

SOFT TISSUE RETRACTOR

CROSS-REFERENCE TO RELATED APPLICATIONS

This application is a divisional application of U.S. patent application Ser. No. 14/425,535 filed on Mar. 3, 2015, which in turn claims priority of U.S. Provisional Application 61/946,986 filed Mar. 3, 2014, both of which are incorporated herein in their entirety by reference.

FIELD OF THE INVENTION

The invention generally relates to the field of spinal orthopedics, and more particularly to tissue retractor devices and blades used to distract soft tissue during surgical procedures.

BACKGROUND

The spine is a flexible column formed of a plurality of bones called vertebrae. The vertebrae are hollow and piled one upon the other forming a strong hollow column for support of the cranium and trunk. Various spinal disorders such as scoliosis, neuromuscular disease, and cerebral palsy may cause the spine to become misaligned, curved, and/or twisted or result in fractured and/or compressed vertebrae. It is often necessary to surgically correct these spinal disorders to straighten or adjust the spine into a proper curvature.

Generally the correct curvature is obtained through surgical procedures by manipulating the vertebrae into their proper position and securing that position with a rigid system of screws, rods, intervertebral spaces, and/or plates. During the surgical procedure, a tissue retractor may be inserted into a surgical incision to pull tissue away from the surgical site thus enlarging the viewing area for the surgeon. Tissue retractors form a surgical corridor including a proximal opening at the incision and a distal opening near the surgical site. Various instruments and implants may be inserted through the corridor. Exemplary tissue retractors may be found in U.S. Pat. No. 7,780,594 entitled "Retractor and Methods of Use" filed Oct. 6, 2006 and U.S. Application Publication Number 2008/0114208 entitled "retractor" filed Sep. 24, 2007.

The amount of tissue to be retracted depends upon the chosen approach as well as various patient characteristics. For example, in a lateral approach, more soft tissue may be present between the surgical incision and the surgical site near the vertebrae than in a posterior approach. Patient anatomical differences may also require various length retractors. The size, shape, and configuration of the retractor may be chosen based on these as well as other factors.

Typical tissue retractors include two or more elongated blades with proximal ends attached to a housing that is in turn attached to a surgical table. Each blade assembly may be attached to a separate portion of the housing and include various adjustment features for manipulating the blades to adjust and enlarge the viewing area. Often, the tissue retractor may hold the blades close together in a tubular configuration for concentric insertion over dilation tubes along a common longitudinal axis. The portions of the housing may translate or rotate relative to one another to gradually pull the blades apart from one another to expand the surgical wound.

When a retractor is opened to distract soft tissue the resistance load pressing on the distal end of the blades increases and causes conical deformation. As used herein "conical deformation" is when the distal end of the blades curve back towards the center of the portal opening forming a cone-like shaped tunnel where the distal opening at the exposed surgical site is smaller than the proximal portal opening. The conical deformation of the blades also causes a reaction force that pushes the retractor away from the surgical site. This requires that the surgeon take extra precaution to prevent the blades from lifting off the bone surface as the retractor is opened.

In order to compensate for blade conical deformation most retractors use a secondary adjustment mechanism. This mechanism typically provides an independent pivot action to cause the distal end of the blade to project further out radially with respect to the proximal end of the blade-a motion referenced herein as "toeing out" or "toe out." The blade may toe out by turning a screw that acts on a lever or by using a biased torsional spring. To properly align the opened retractor the surgeon is required to make two independent adjustments for each blade requiring additional surgical time, and adds complexity and bulk to the jaws of the retractor. Due to the limited area available in the jaw area the adjustment mechanisms must be compact which limits the leverage available to counteract the torque generated by long length blades. This lack of adequate counter leverage leads to very large loads that are applied to small mechanisms. Failure and wear of the secondary blade mechanism is a common complaint for such retractors. Accordingly, there exists a need in the art to provide a soft tissue retractor that adequately compensates for the conical deformation of the blades during a procedure.

Furthermore, successful surgery is performed when using these retractors by preventing soft tissue from encroaching into the surgical site by slipping under the distal end of the blade. The prime factor in managing the dissection of soft tissue is maintaining contact of the distal end of the blades with the surface of the bone to prevent tissue encroachment. However, maintaining blade contact is difficult because the bone structure has a complex surface geometry that may cause the blade to lift as the blades are spread apart.

To reduce the risk of complications, current retractor systems rely on docking and stabilization of the retractor rigidly with at least one surgical table arm. It is often necessary for the surgeon to remove and replace a blade with a blade of a different length to accommodate the varying bone structure. This replacement is often required at the L4/L5 disc space where the retractor frame may have to be tilted to avoid contact with the iliac crest. Replacing a blade during a procedure adds time.

Adjustment mechanisms of the prior art have attempted to address the blade contact issue by the use of shims that project beyond the end of the blade and contact the bone surface. The shims are fit into a groove in the blade and slide down the entire length of the blade. This structure provides the disadvantage of requiring the use of a separate component that has to be mounted to an insertion instrument.

Another system to provide blade adjustment is the use of a telescoping blade that uses a nested blade that can be extended to the required length. However, this method of using nested blades increases the blade cross-sectional area causing a more bulky blade system that requires larger initial dilation and increased tissue expansion for an aperture during a procedure.

Accordingly, there exists a need in the art to provide a soft tissue retractor providing for depth adjustment to prevent encroachment of soft tissue during a procedure.

SUMMARY OF THE INVENTION

Provided herein are retractors configured to compensate for blade conical deformation, and a blade having an adjustment mechanism configured to adjust the depth of the blade so as to reduce the need for a shim.

In one embodiment, a tissue retractor includes a frame having at least one cam. The at least one cam is operatively connected to at least one cam follower. The cam follower may be a flat surface of a lever. The lever has a blade. The blade is disposed on a distal end of the lever, and is generally orthogonally to the lever and is in a fixed relationship to the cam follower. In some instances, the tissue retractor has at least two levers and each lever has a blade disposed on a distal end. The cam follower follows the cam so as to drive a distal end of respective blades away from each other as a respective proximal end of the at least two levers are squeezed towards each other. Accordingly, squeezing the levers together simultaneously opens a surgical corridor and causes the blades to toe out.

The frame may include a flange extending away from the frame towards the levers. The cam is mounted to the flange. The cam is mechanically coupled to a portion of a lever and is configured to guide the lever along an arcuate path so as to move the distal end of the blades away from each other. The arcuate path is generally orthogonal to a diameter of the surgical corridor. The curved geometry of the outer surface of the cam permits the rotation of the cam follower abutting the cam to result in rotation of the blade. Accordingly, a pair of cam followers bias against a pair of cams and the distal ends of the blades toe-out to compensate for blade conical deformation. The arcuate path is disposed generally along a radius generally orthogonal to the respective levers, and accordingly, the distal end of a blade travels radially further than the proximal end of the blade when the levers are squeezed together.

In other embodiments, the cam follower is directly connected to an arm of a ring retractor. Knobs corresponding with each arm and blade are adapted to rotate the arms and urge the cam followers along the cam to produce toe-out.

One example embodiment includes a frame with a plurality of flanges. Yet in another embodiment, the frame is a ring structure having a plurality of bores. Accordingly, the cam and cam follower automatically compensate for the increasing load on the distal ends of the blades when the blades are expanded in the tissue.

A blade having a blade adjustment mechanism allowing for adjustment of the depth of the blades of the tissue retractor is also provided. In such an embodiment, the retractor includes a lever having a housing adapted to connect with the adjustment mechanism. The adjustment mechanism includes a threaded portion formed on the blade. The adjustment mechanism further includes an adjustment screw, at least a portion of the adjustment screw is threaded, and the adjustment screw connects the blade to the lever. The threaded portion of the blade is mechanically coupled to the threaded portion of the adjustment screw wherein rotation of the adjustment screw displaces the blade in a vertical arrangement thereby allowing for adjustment of the depth of the blade. Furthermore, a spring loaded lock is connected to the threaded portion of the adjustment screw, the lock movable with the adjustment screw during depth adjustment.

Accordingly, the blades may be adjusted in depth so as to eliminate the use of shims. Further, the depth adjustment mechanism is disposed on the blade itself and integrates with the blade locking mechanism thereby minimizing the size of the retractor so the surgeon has the maximum amount of visualization when taking photos or performing a procedure.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

FIG. 3 is a perspective view of the first position of one embodiment of the tissue retractor shown in FIG. 1;

FIG. 4 is a perspective view of the second position of the tissue retractor shown in FIG. 1;

DETAILED DESCRIPTION OF THE INVENTION

A retractor configured to compensate for blade deformation is provided. A blade having an adjustment mechanism is also provided. The blade is configured to mount to a housing of a lever so as to adjust the depth of the blade.

In a first embodiment, the tissue retractor includes a frame having at least one cam. The cam is operatively connected to a cam follower. The cam follower and a lever are in a fixed relationship with respect to each other. A blade is fixedly mounted to the distal end of the lever and is generally orthogonally to the lever. Accordingly, the blade is also in a fixed relationship with the cam follower.

In some instances, the tissue retractor has two levers and squeezing the levers results in simultaneous opening and "toeing-out" of the blades. Namely, each lever urges a cam follower along a cam so as to drive a distal end of the blades away from each other as the surgical corridor is formed. Each cam is mechanically coupled to a given blade and includes a curved surface configured to guide a given cam follower and the blade wherein the blade may compensate for the load exerted by the tissue. In another embodiment, two offset cams are provided to facilitate the toe-out motion. The tissue retractor eliminates the need for bulky secondary blade mechanisms to counteract undesired blade deformation at the surgical site.

Unless defined otherwise, all technical and scientific terms used herein have the same meaning as commonly understood by one of ordinary skill in the art. It must also be noted that as used herein and in the appended claims, the singular forms "a," "an," and "the" include plural reference unless the context clearly dictates otherwise. Thus, for example, reference to a "lever" is a reference to one or more levers and equivalents thereof known to those skilled in the art, and so forth.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards a surgical area of a patient and/or the implant.

Figure 1:
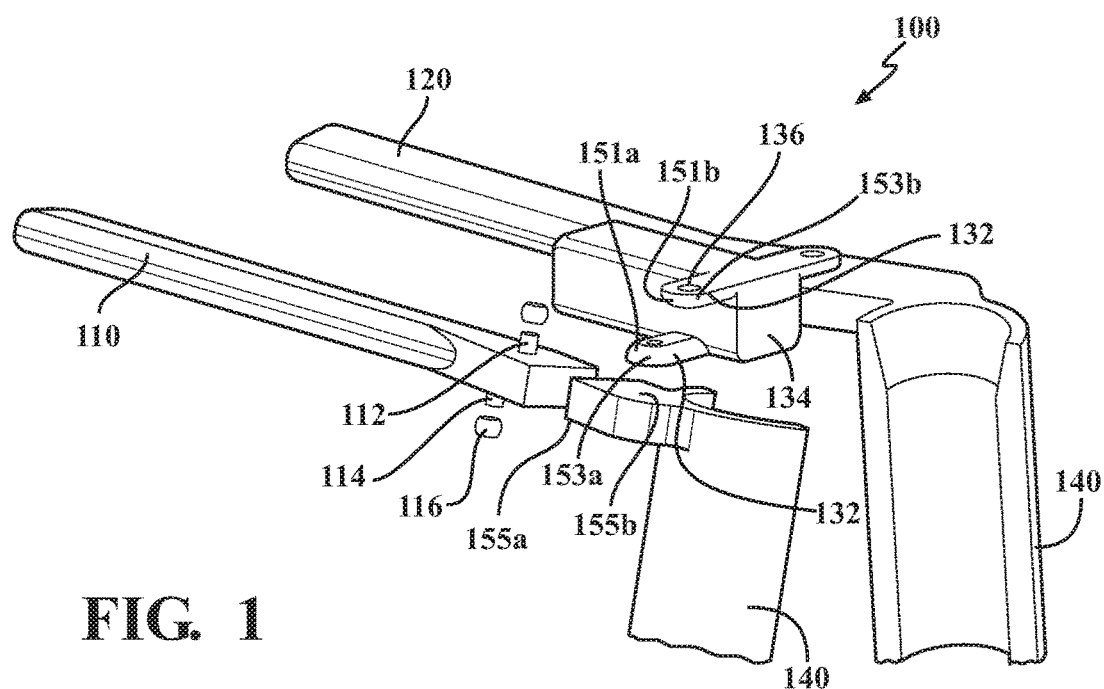
FIG. 1 is an exploded perspective view of one embodiment of the tissue retractor.

Now referring to FIG. 1, a tissue retractor having at least two levers is provided. The lever actuated tissue retractor 100 includes a first lever 110, a second lever 120, a frame 134, and a plurality of blades 140. As shown in FIG. 1 the tissue retractor 100 includes a cam 151 having a cam surface 153. FIG. 1 shows the tissue retractor having two pair of cams 151, i.e. an upper cam 151a and a lower cam 151b, operatively coupled to each lever 110, 120. The pair of cams 151a, 151b are offset each other on a respective side of the frame 134. Each cam 151a, 151b includes respective cam surfaces 153a, 153b for which a respective cam follower 155a, 155b follows. However, it should be appreciated that the illustrations provided herein are not limiting to the scope of the appended claims and that the tissue retractor may be configured to have only one cam 151 on each side of the frame 134 coupled to a respective lever 110, 120. In such an embodiment where only one cam 151 is used, it should be appreciated that the geometry of the cam surface 153 along with the positioning of the cam 151 with respect to the blade 140 and the length of the blade 140 will determine the arc length and the range of motion of the toe-out of the distal end of the blade 140.

The cam surface 153 is mechanically coupled a respective cam follower 155. The cam surface 153 is generally curved and configured to generate a toe-out movement of the blade 140. The blades 140 may be opened and closed relative to each other by squeezing the first lever 110 and second lever 120 towards each other. It should be appreciated that, operation of one cam and cam follower need only be described, as the operation of the other cam and cam follower is the same.

The cam 151 is mechanically coupled to a cam follower 155. The cam follower 155 is generally disposed at the proximal end of the blade 140. The cam 151 includes a curved cam surface 153 for which the cam follower rides 155 along and is guided along the path of the cam surface 153. Accordingly, the blade toes outs so as to compensate for the load exerted by the tissue. In one embodiment, two offset cams 151 are provided to facilitate the toe-out motion.

The cam follower 155 is urged along respective cams 151a, 151b and cam surfaces 153a, 153b. In other embodiments, a plurality of cams 151 are provided. In this embodiment, the cam follower 155 directly connects to the cam 151 without the use of pivot posts and spherical elements (such as discussed below). The cam follower is adapted to connect and move directly on the cam surface 153.

The cam follower 155 is operatively connected to the cam surface 153. FIGS. 1-6 provide an illustrative example of a means for connecting the cam follower 155 to the cam 151. A first pivot post 112 and a second pivot post 114 extend from opposing surfaces of a lever 110, 120. A plurality of spherical elements 116 are disposed at the distal end of the pivot posts. In this particular embodiment, the spherical elements 116 are spherical bushings that surround the distal end of the first pivot post 112 and the second pivot post 114. The pivot posts 112, 114 and the spherical elements 116 help facilitate the connection between the cam 151 and the cam follower 155.

Figure 5:
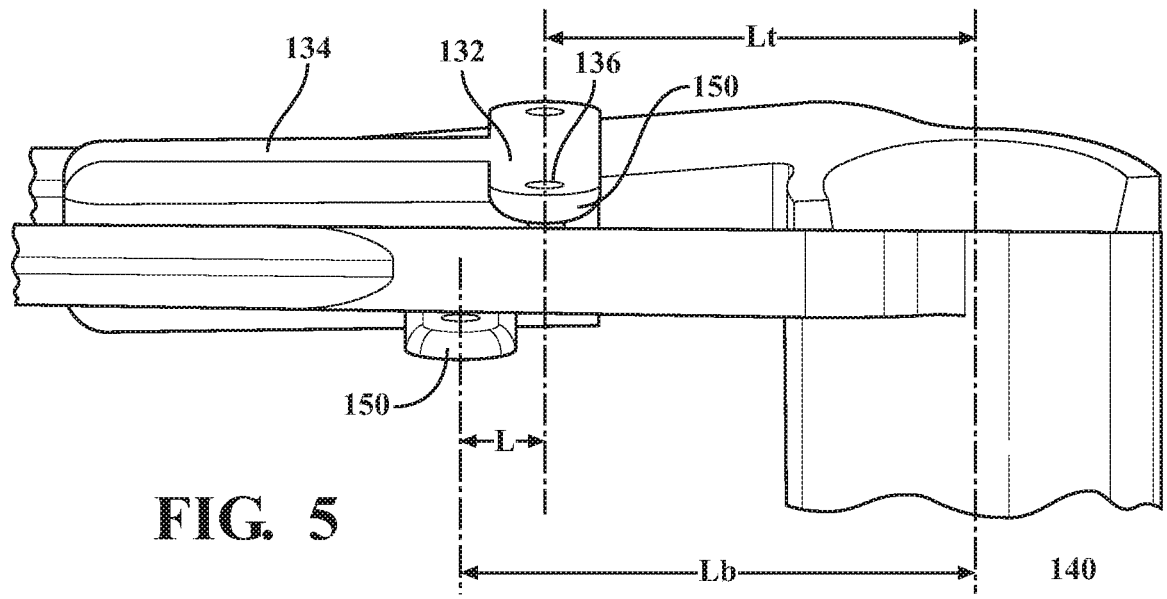
FIG. 5 is an isolated view of the offset cams of the tissue retractor shown in FIG. 1.
Figure 6:
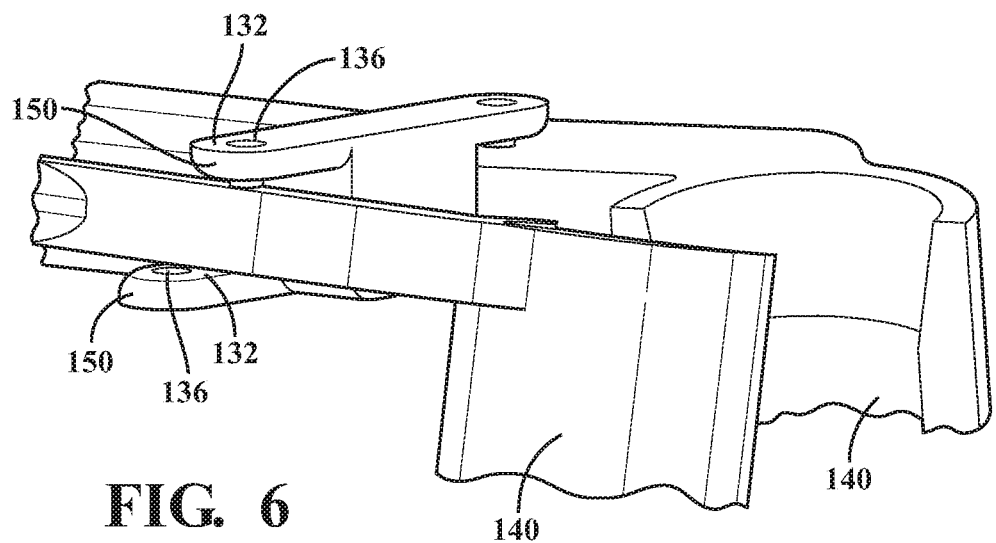
FIG. 6 is a close up perspective view of the tissue retractor shown in FIG. 1 illustrating the offset cams.

The first pivot post 112 and the second pivot post 114 are offset in relation to one another in the same offset relation as the respective cams 151. The first pivot post 112 and the second pivot post 114 also are offset in relation to one another in a distal and proximal direction along a portion a length of the first lever 110 by an offset length L, such as shown in FIG. 5. The first post 112 is disposed distal to the second post 114 by offset length L. As shown in FIG. 1 the first and second pivot posts are disposed near the distal end of the first lever 110. Also shown in FIG. 1 is the second lever 120. The second lever 120 may be a mirror image of the first lever 110 with corresponding pivot posts, spherical elements 116, cam 151, cam surface 153 and cam followers. In other embodiments not shown, the second lever 120 may not be a mirror image of the first lever 110 such as having a different offset length between the pivot posts. In yet other embodiments, the second lever 120 may be an elongated extension of frame 134 or otherwise attached to frame 134 such that the lever is immobile.

The frame 134 includes a plurality of flanges 132 extending outwardly from opposite sides of the frame 134. The plurality of flanges 132 are positioned such that the first lever 110 and the second lever 120 can be positioned in a space between the flanges 132. Furthermore, the flanges 132 have pivot sockets 136 corresponding to the first pivot post 112 and second pivot post 114 for both the first lever 110 and second lever 120. The cam surface 153 is disposed on the distal end of the respective flanges.

Figure 2:
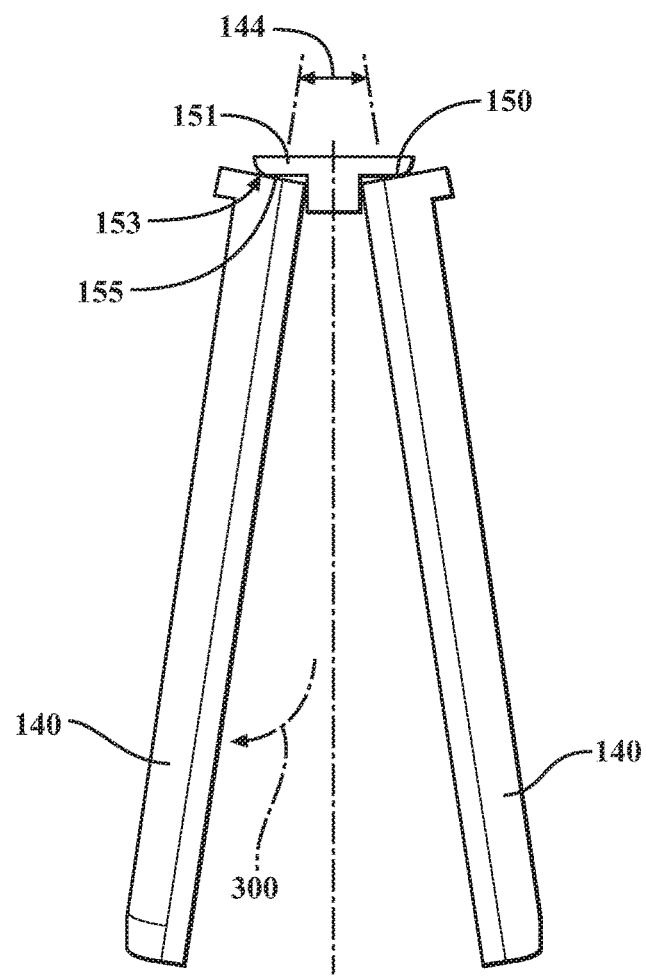
FIG. 2 is a front view of the tissue retractor shown in FIG. 1.

In one embodiment the pivot sockets 136 house the spherical elements 116 to create a plurality pivot points 150 that are ball-and-socket joints as shown in FIG. 2. The pivot points 150 in this particular embodiment are ball-and-socket joints and thus providing independent and multi-axial movement at each pivot point 150 allowing the cam follower 155 to follow the arcuate path of the cam surface 153. In embodiments not shown, the pivot posts may be cast or welded with spherical elements 116.

In another embodiment not shown, the plurality of flanges 132 may extend along the length of the frame 134. Although the flanges 132 of the exemplary embodiment of FIG. 1 extend away from the frame 134 at right angles, one of ordinary skill in the art necessarily understands that various flange geometries can be implemented provided that the flange provides proper structural support for the offset pivot points 150 and the desired lever motion.

A plurality of blades 140 shown in FIG. 1 are attached to the distal ends of the first and second levers 110. 120. In other embodiments, only one (or more than two) blade(s) 140 are used. The blades 140 may be attached by welding or may be cast as a continuous extension from a given lever.

The plurality of blades 140 may be positioned at any angle relative to the first and second levers 110, 120. In this particular embodiment shown in FIG. 1, the plurality of blades 140 are perpendicular to the first and second levers 110, 120. In other embodiments, the plurality of blades 140 may have a more acute or more obtuse angle.

The plurality of blades 140 in a first position form a surgical corridor, which may be used with other medical instruments such as, for example, a dilator. In the first position, the blades 140 may be inserted over the dilator. As the proximal ends of the first lever 110 and second lever 120 are squeezed together, the distal ends of the levers will simultaneously spread apart and rotate in a multi-plane motion causing the top and bottom sides of the levers 110, 120 to follow separate arc lengths and provide simultaneous opening and toeing action to the plurality of blades 140. Movement of the plurality of blades 140 away from each other will result in opening the surgical corridor and in a toe angle 144 in a second position, as shown in FIG. 2. The offset length L between the cams determines an opening angle 142 and toe angle 144. The amount of toe angle 144 generated is a sinusoidal relation to the opening angle 142 which increases in gain as the opening angle increases.

The length L of pivot offset as shown in FIG. 5 can be adjusted to adjust blade deflection so that a parallel or a toed out condition will exist when the blades are fully opened. The bottom arc length Lb and the top arc length Lt (shown in FIG. 5) may also be adjusted to adjust blade deflection. Deflection is the amount that the blades are displaced axially with respect to each other. Specifically, the amount the blades are displaced during a procedure when soft tissue exerts a force against the blades.

The illustrative embodiments described depict uniform sized spherical elements 116 and pivot pocket opening sizes. It is necessarily apparent to one of skill in the art that various combinations of spherical element 116 size, pivot pocket opening sizes, cam surface geometry and cam follower geometry may be implemented to achieve the desired opening angle and tilt angle required for various circumstances.

In an embodiment not shown, the lever actuated tissue retractor device 100 may also include a biasing mechanism to return the plurality of blades 140 to the first position (FIG. 4) or may be biased to return the plurality of blades 140 to the second position (FIG. 3). For example, a spring may be positioned between the first lever 110 and second lever 120 such that upon relieving the compression force the levers will actuate the tissue retractor device to the first position.

Also not shown, is an embodiment that includes a lock mechanism displaced between the levers that can retain one or more open positions. In one embodiment, the lock mechanism can be a ratchet assembly. In another embodiment the lock mechanism can be opposing elongated members with corresponding serrations that interact to retain an open position. In yet another embodiment, the lock mechanism is combined with the biasing mechanism such that the tissue retractor device will automatically close with the release of the lock mechanism or vice versa automatically open with the release of the lock mechanism. Alternatively, the lock mechanism can be similar to the lock mechanism illustrated in FIGS. 22-29.

Furthermore, the illustrative embodiment described changes to the geometry of the cams 151 along one axis. However, one of ordinary skill in the art necessarily understands that the geometry of the cams 151 may be changed along two axes to tailor the path of the tilting motion relative to the blade opening as desired. Along with the geometry of the cam surface 153, the length of the plurality of blades 140 will determine the arc length exhibited by the distal ends of the blades 140 as well as the amount of torque required to displace the tissue at the surgical site. Thus, blades of various sizes both uniform and non-uniform are contemplated within the scope of the present invention.

Figure 22:
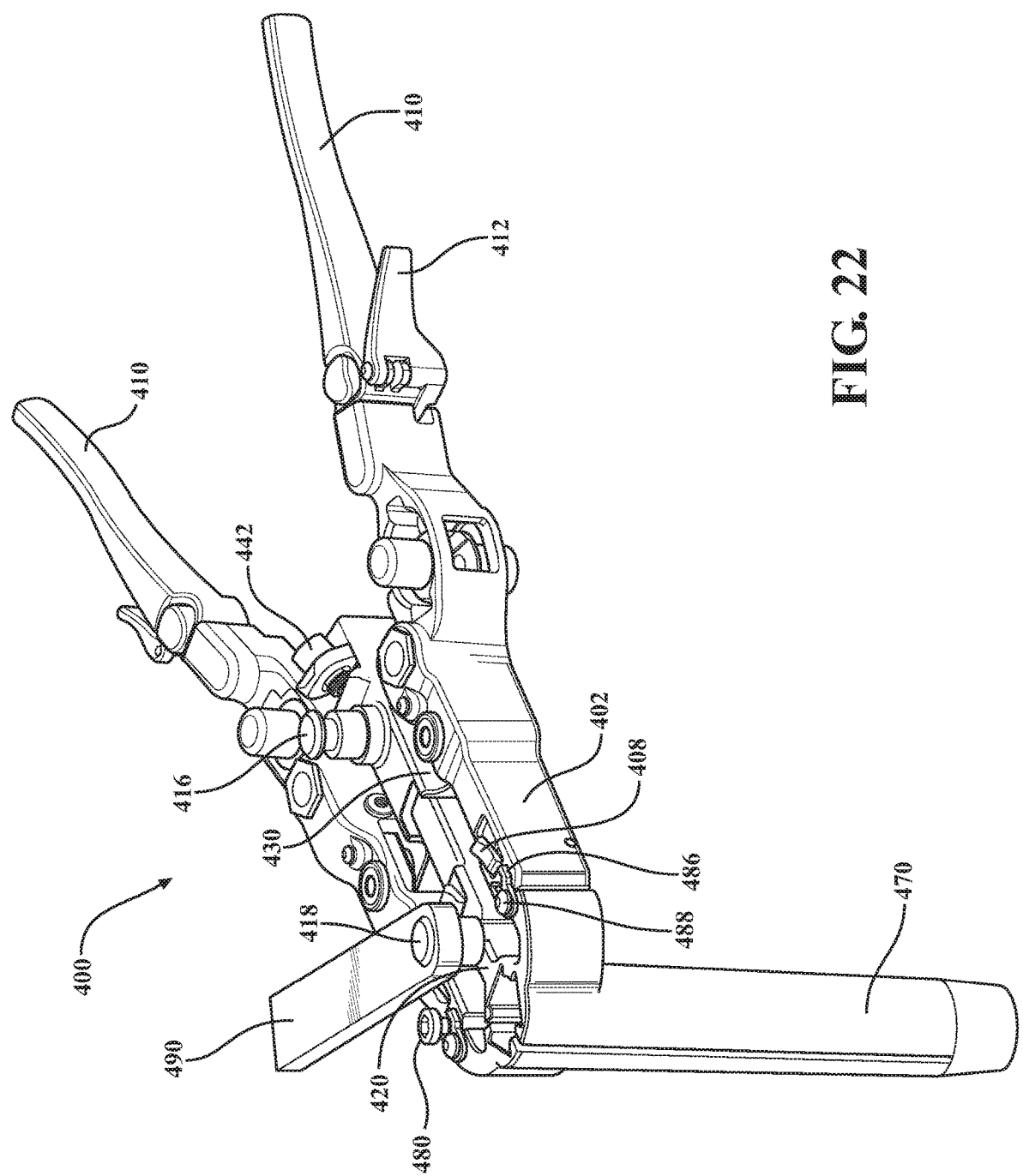
FIG. 22 is a perspective view of one embodiment of a tissue retractor and a blade with a depth adjustment mechanism.
Figure 23:
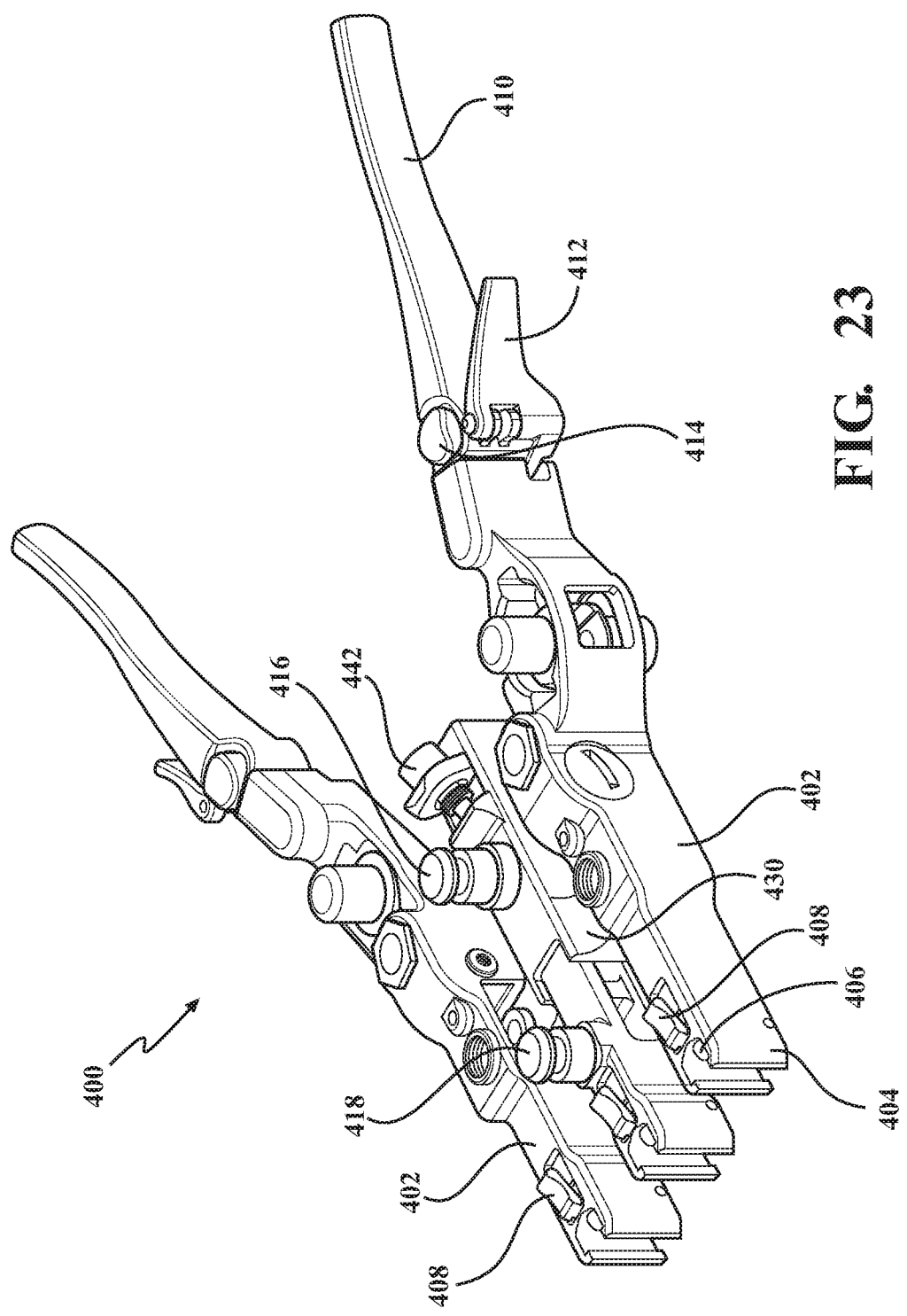
FIG. 23 is a perspective view of the tissue retractor shown in FIG. 22 with the blades removed.
Figure 24:
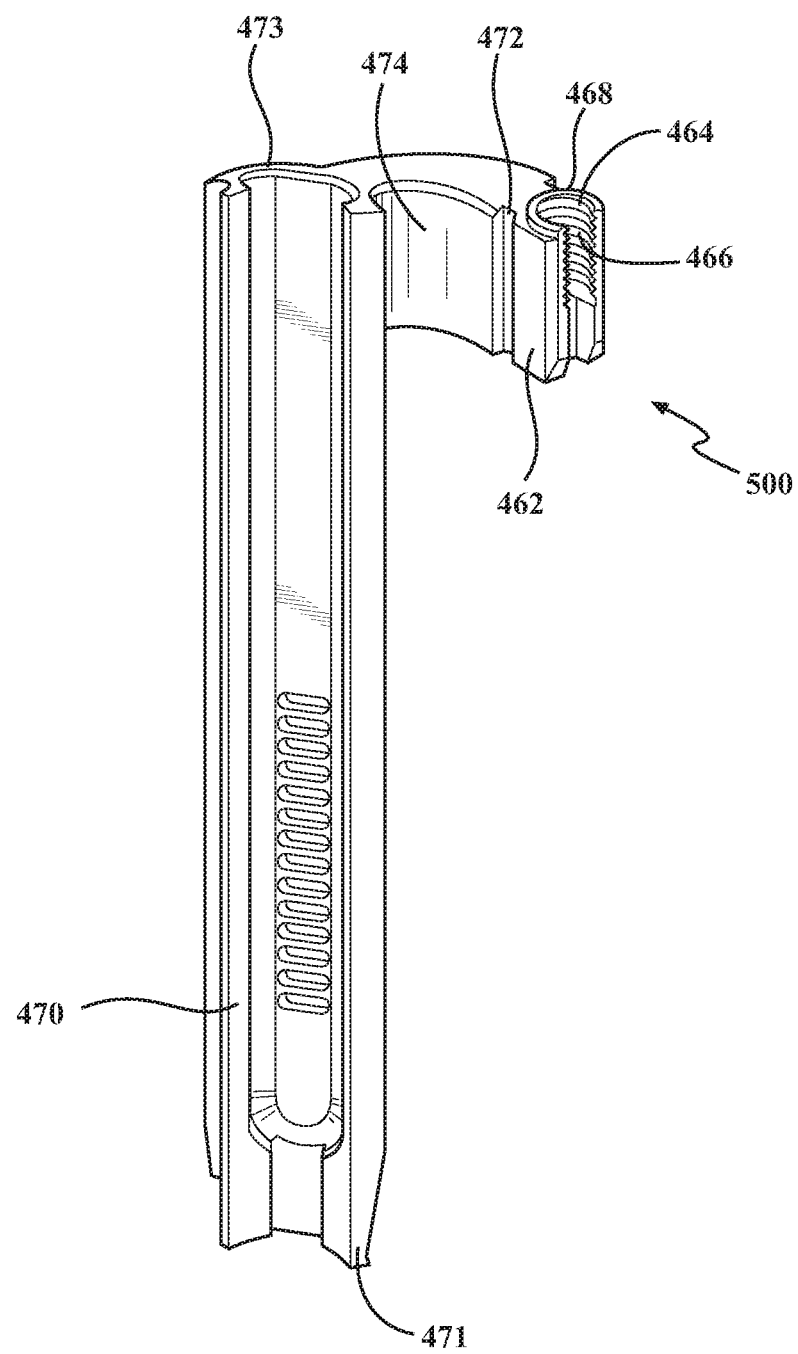
FIG. 24 is a perspective view of a blade.

It should also be appreciated that the tissue retractor 100 may include multiple blades 140. For example, the cam 151 and cam follower 155 may be used in a three blade 140 configuration by having a central blade (or posterior blade) mounted to the frame 134. This embodiment would be similar to the blade configuration as shown in FIG. 22.

Figure 7:
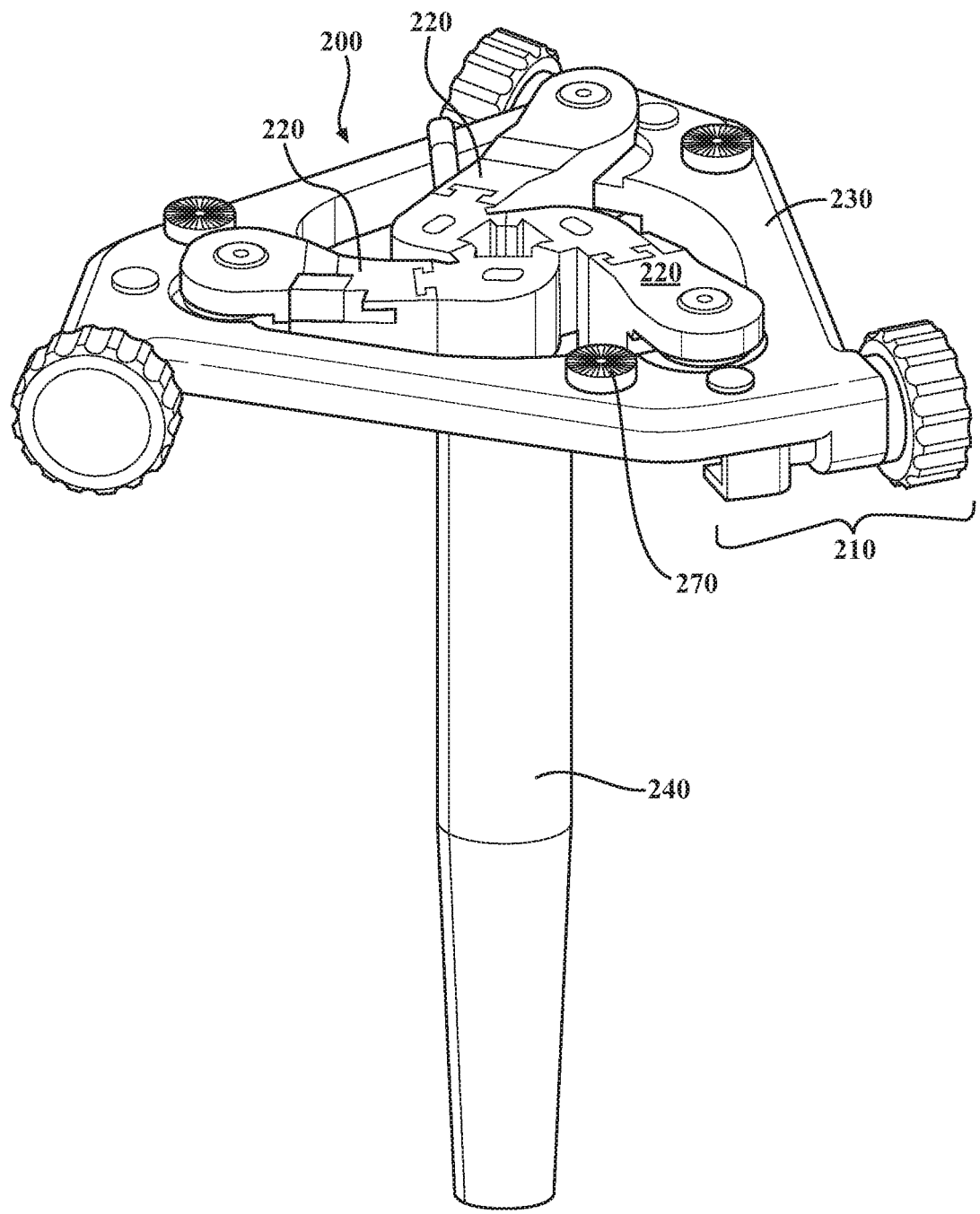
FIG. 7 is a perspective view of another embodiment of a tissue retractor having a ring frame.
Figure 8:
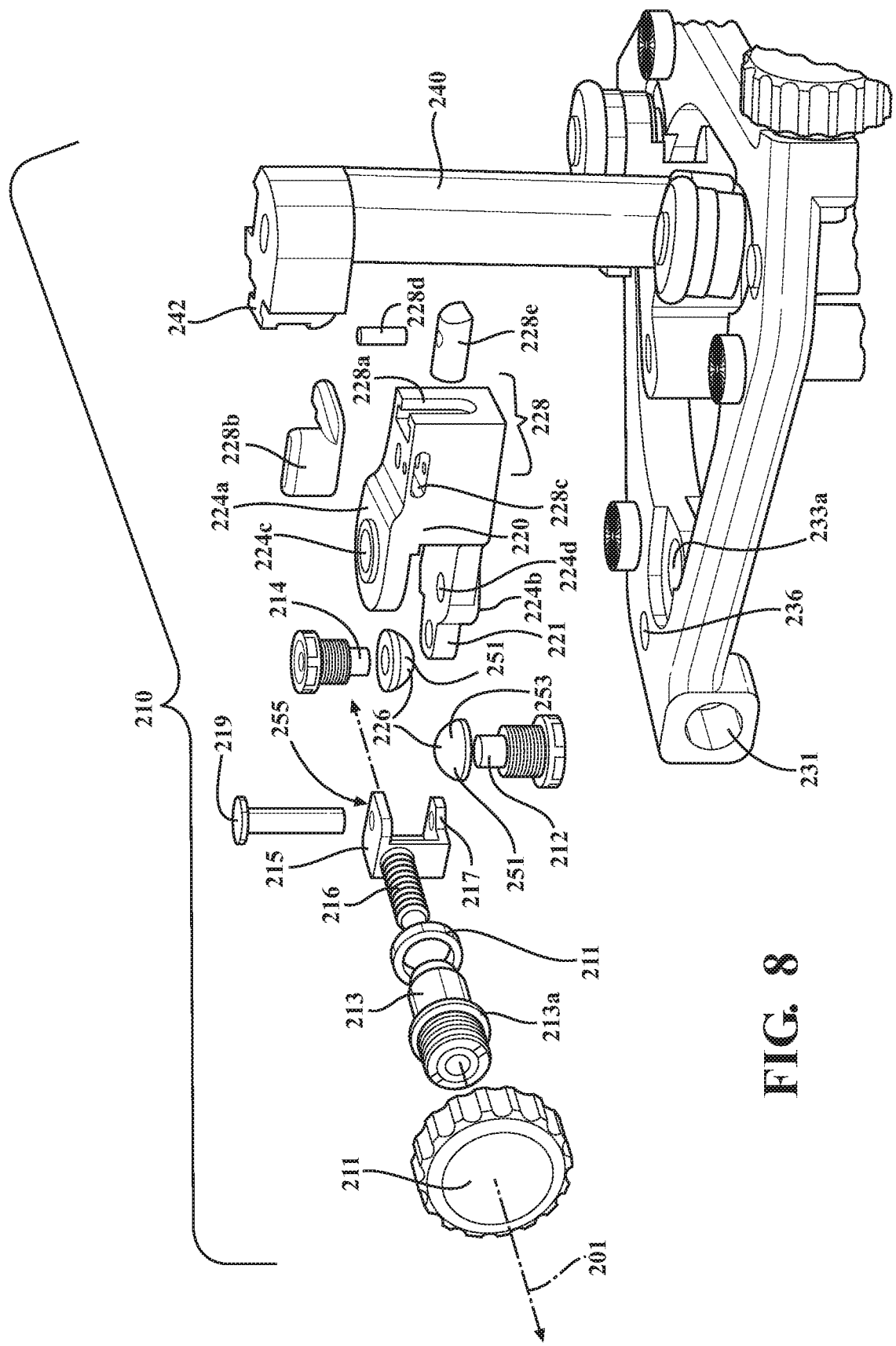
FIG. 8 is an exploded of the tissue retractor shown in FIG. 8.

Now referring to FIG. 7 another embodiment of a tissue retractor 200 having a ring frame 230 is provided wherein the like elements are referenced by like numbers increased by 100. The tissue retractor 200 includes the ring frame 230, a plurality of drive assemblies 210, at least one arm 220 and a plurality of blades 240. Each blade 240 is connected in a generally orthogonal arrangement to a respective arm 220. The tissue retractor 200 includes at least one cam 251 and respective cam surface 253 (FIG. 8). A cam follower 255 is coupled to the cam surfaces 253 of the cam 251.

The cam 251 includes the cam surface 253 which is curved along a radius generally orthogonal to the plane of the ring frame 230 and thus is configured to guide a respective blade 240 to toe out wherein the blade 240 may compensate for the load exerted by the tissue.

The cam 251 and cam follower 255 are coupled together by a first and second pivot post. The first and second pivot post 212, 214 allow the cam follower 255 to rotate, move and pivot about the cam surface 253. Accordingly, the cam follower 255 may follow the cam surface 253.

In this embodiment, the cam follower 255 connects to an arm 220. The arm 220 includes a blade 240 fixedly mounted to a free end of the arm 220. The arm 220 is configured to swing inwardly within the ring frame 230. As the arm 220 swings inwardly, the cam follower 255 follows the cam surface 253 resulting in a toe-out motion of the blades 240.

The ring frame 230 may also include a boss 270 to enable the attachment of the ring frame 230 to a stabilization surgical arm (not shown). The stabilization surgical supports the retractor during surgery.

An illustration of a drive assembly 210 is shown in FIGS. 7 and 8. The drive assembly 210 includes a knob 211 coupled to barrel 213 by having internal threads corresponding to the threads on the proximal end of barrel 213. In other embodiments, the knob 211 is coupled as a snap on piece to the proximal end of barrel 213 or the knob 211 may be glued, welded, or cast as part of barrel 213.

The barrel 213 is retained in bore 231 which essentially acts as a bushing allowing barrel 213 to rotate around a longitudinal axis 201. As such, barrel 213 may include bearings or any other structure that is conducive to rotation. The diameter of bore 231 is such that the rotation of barrel 213 remains substantially on a single longitudinal axis 201.

The distance between collar 213a and detachable collar 211 is such that the lateral movement of barrel 213 is prevented.

The barrel 213 has internal threads that correspond to the threads on a clevis engagement piece 216 such that rotation of barrel 213 actuated by knob 211 results in the translation of the rotational movement of barrel 213 to lateral movement of the clevis engagement piece 216 and the clevis 215 in the proximal and distal direction along longitudinal axis 201. In other embodiments not shown, lateral movement of the clevis may not require a threaded barrel. For example, knob 211 may have a central bore with corresponding threads to clevis engagement piece 216 obviating the need for a threaded barrel. In other embodiments of the drive assembly 210, the knob 211 may be omitted and instead the clevis engagement piece 216 may be elongated threaded piece or a rack such that the clevis 215 can be actuated by a ratcheted pinion or coupled to another device. It is necessarily apparent to one of ordinary skill in the art that the drive assembly 210 embodiment for imparting the described motion is only for illustrative purposes, and all structures that impart similar motions are contemplated within the scope of the present invention.

The clevis 215 is coupled to the arm piece 220 via a pivot pin 219 hinging a clevis knuckle 217 with an arm piece knuckle 221 to create an elbow-like joint or hinge. The pivot pin 219 in this particular embodiment passes through a track 236 to facilitate controlled movement of clevis 215 along longitudinal axis 201. The pivot pin 219 in other embodiments not shown may be a quick pin or any similar type of pin which enables detachability of the arm piece 220. The clevis 215 in this particular embodiment incorporates a yoke-type conformation wherein the arm piece knuckle 221 is disposed within the clevis knuckle 217. The pivot pin 219 is passed through the clevis 215 and knuckle 221, thereby securing the clevis 215 to the knuckle. The knob 211 may be rotated so as to urge the clevis 215 forward, however the pin 219 translates the forward advancement of the clevis 215 into rotational movement, wherein the knuckle 217 and the arm piece 220 swing outwardly as one piece, carrying the blade 240. In other embodiments not shown, the pivot pin 219 may be a grommet wherein the clevis knuckle 217 does not have the yoke-like conformation as shown in FIG. 7. Other embodiments wherein the clevis knuckle 217 does not have a yoke-like conformation are fully contemplated within the scope of the present invention provided that the desired hinge can be achieved.

The arm piece 220 in this embodiment includes a first pivot post 212 and second pivot post 214 which are offset from each other. The first pivot post 212 includes the cam 251 having a generally curved surface. The second pivot post 214 includes the cam follower 255 having a generally curved surface. The cam 251 is fixedly mounted to an end portion of the first pivot post 212 and the cam follower 255 is fixedly mounted to an end portion of the second pivot post.

Figure 9:
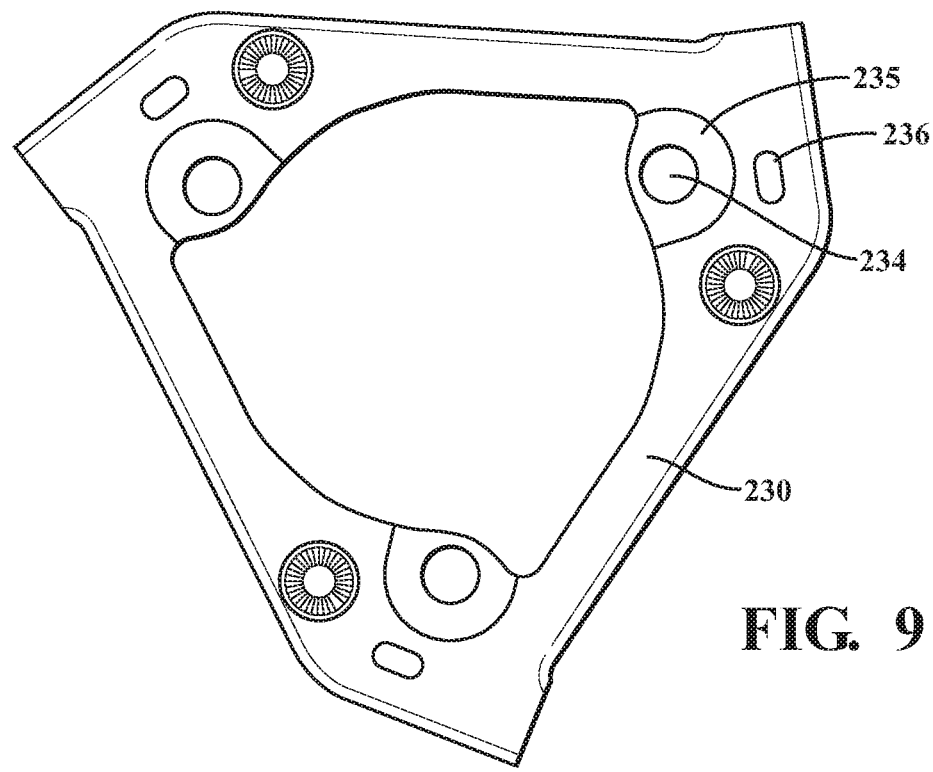
FIG. 9 is a top view of the ring frame shown in FIG. 7.
Figure 10:
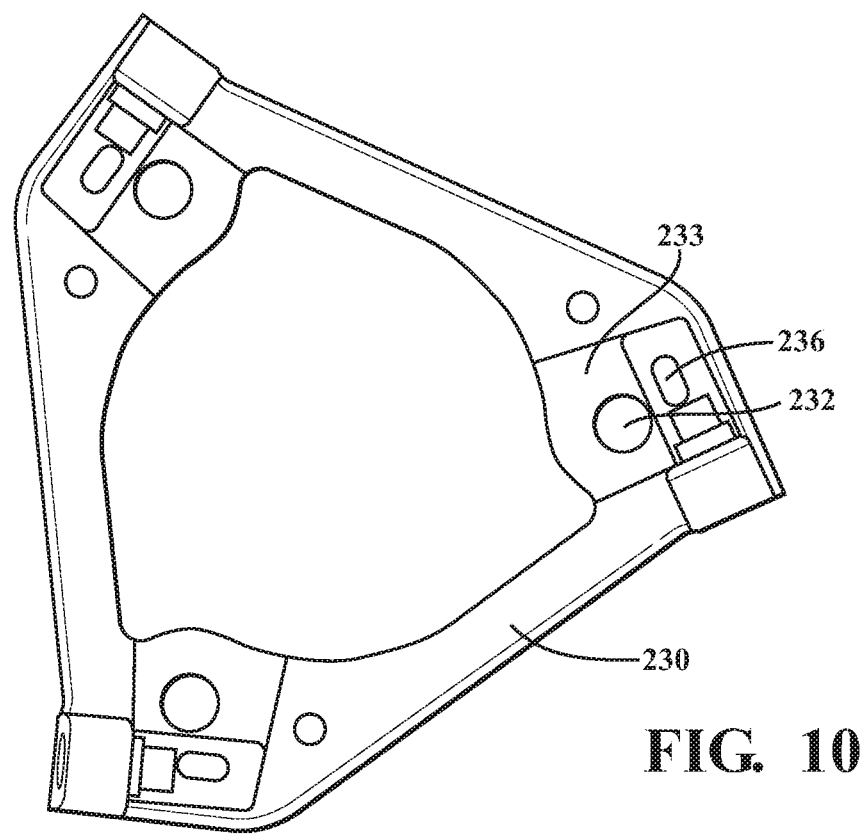
FIG. 10 is a bottom view the ring frame shown in FIG. 9.
Figure 12:
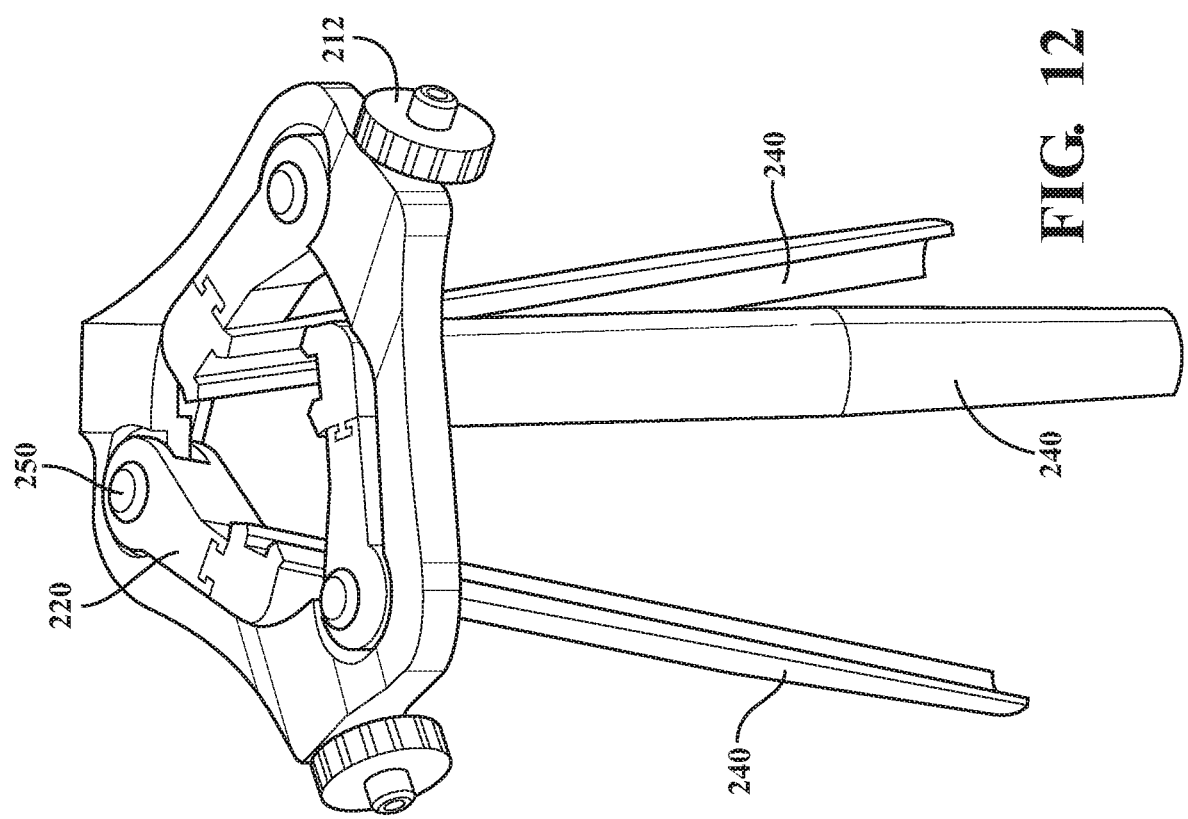
FIG. 12 is a perspective view of the tissue retractor shown in FIG. 7 in a second position.
Figure 11:
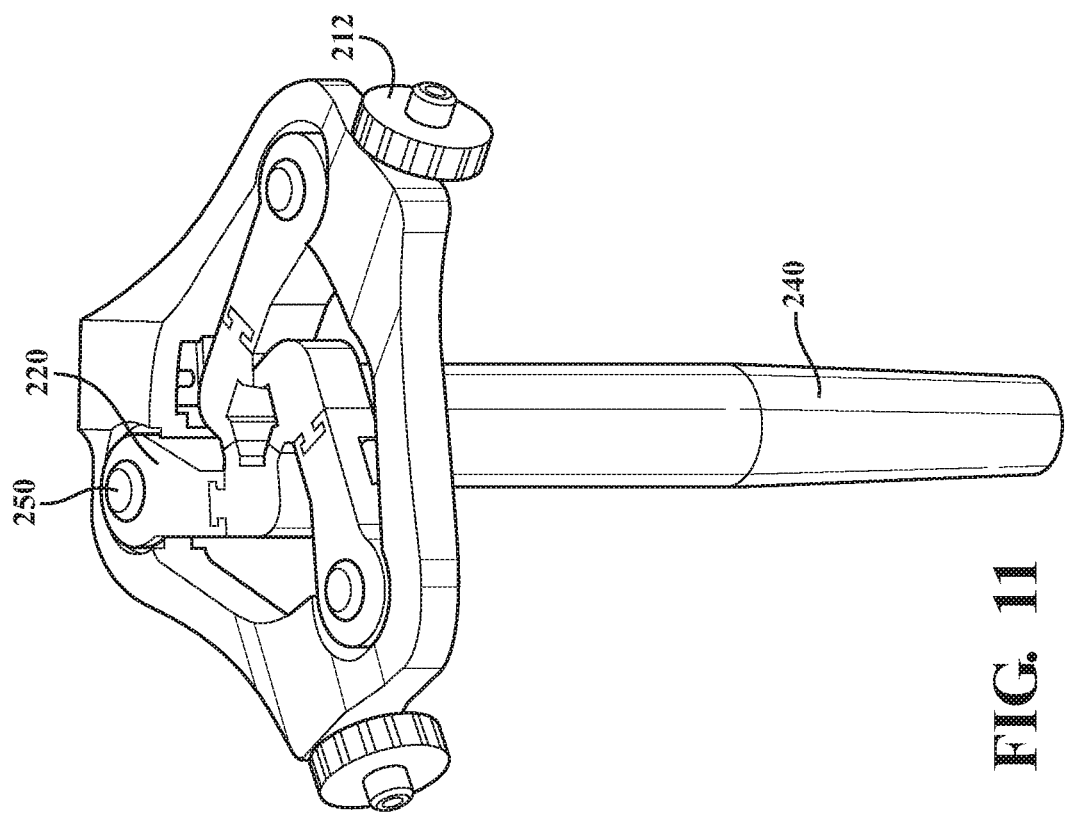
FIG. 11 is a perspective view of the tissue retractor shown in FIG. 7 in a first position.

Now referring to FIGS. 9 and 10 which illustrate the bottom view of ring frame 230 and FIG. 9 which illustrates the top view of ring frame 230, the arm piece 220. The first and second spot face 233, 235 have an aperture 233a through which the first pivot post 212 passes through. The arm piece 220 has a yoke-like structure with two prongs 224a, 224b having respective apertures 224c, 224d (FIG. 8). The spot faces 233, 235 fit within the prongs 224a, 224b of the arm piece 220. The first and second pivot posts 212, 214 are inserted into respective apertures 224c, 224d. The apertures 224c, 224d are offset from each other with respect to a longitudinal axis of the arm piece 220. Aperture 224d is aligned with aperture 233a wherein the first pivot post 223 is mounted therein. The end of the first pivot post 212 includes a cam 251 having a cam surface 253 and the end of the second pivot post 214 includes a cam follower 255. The cam 251 and cam follower 255 are disposed within the interior of the yoke-like arm piece 220. The cam 251 and cam follower 255 may or may not each have a threaded bore configured to receive threaded ends (not shown) of respective first and second pivot posts 212, 214 so as to couple the arm piece 220 to ring frame 230 such that the cam 251 and cam follower 255 are mounted to their corresponding pivot sockets wherein the cam follower 255 is pressed against the cam surface 253. Accordingly, opening of the blade 240 urges the cam follower 255 along the arcuate path of the cam surface 253 causing the distal end of the blade 240 to toe out as the blade 240 is opened. It should be appreciated that the blade 240 may be opened by rotating knob 211 as described above.

The tissue retractor 200 may further include a blade locking mechanism 228 by which the blade 240 is coupled to the arm piece 220. In the example embodiment shown in FIGS. 8 and 20, the blade locking mechanism 228 includes a slot 228a, a latch 228b, a latch slot 228c, a locking pin 228d, and a set pin 228e. The engageable end of latch 228b is inserted into latch slot 228c and coupled to the locking pin 228d by disposing a set pin 228e through aligned openings on the latch 228b and locking pin 228d. The latch 228b or locking pin 228d is biased such that the locking pin 228d protrudes into the stub receiving slot 228a until the latch 228b is actuated to withdraw the locking pin 228d from the stub receiving slot 228a. The distal end of the locking pin 228d is angled as shown in or rounded such that a blade tang 242 can slide into the stub receiving slot 228a and be secured as the locking pin 228d sets into a notch on the blade tang 242. In other embodiments not shown, the blade is welded or is part of a continuous cast of the arm piece 220.

Figure 17:
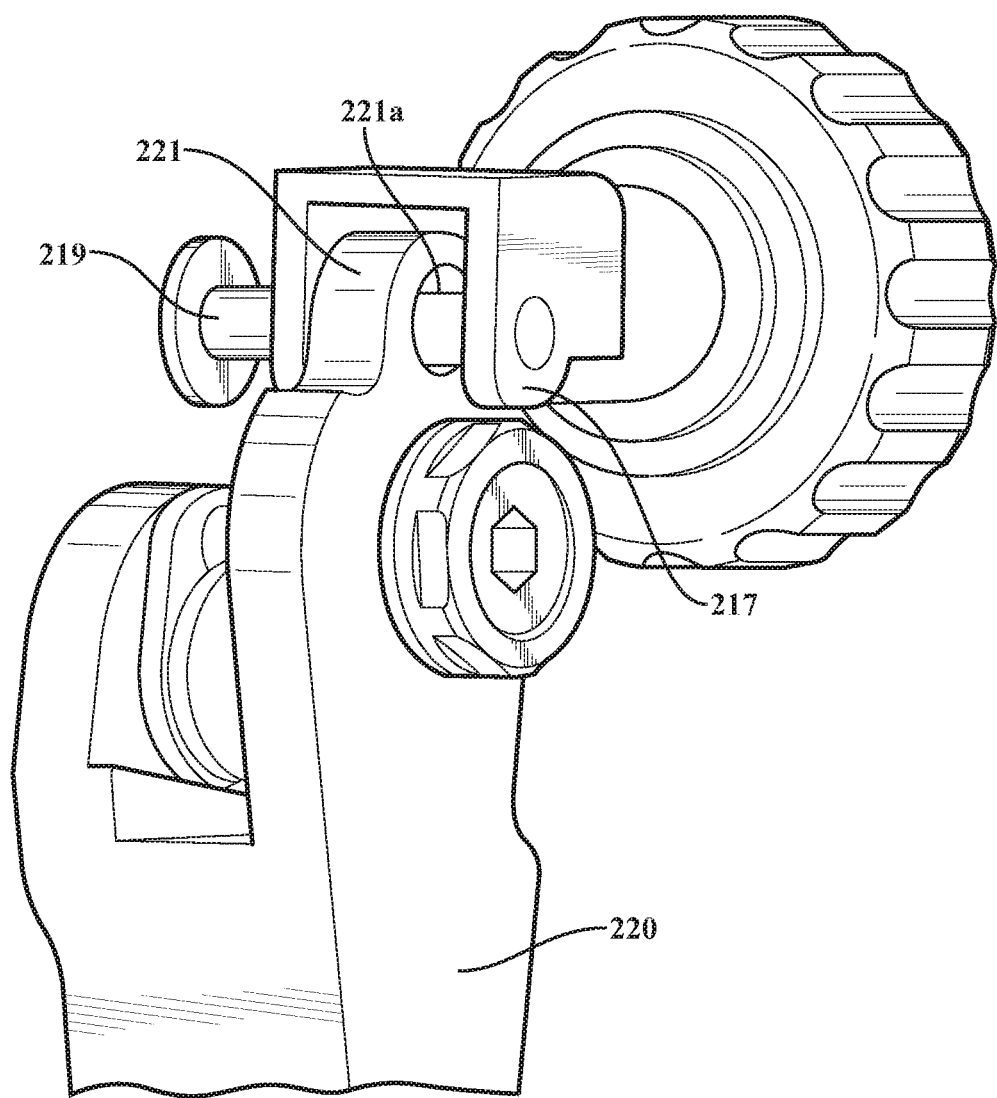
FIG. 17 is a close up perspective view of a hinge.

An isolated view of the arm piece knuckle 221 attachment point 221a and clevis 215 is provided in FIG. 17. The ring frame 230 is purposefully omitted to show that the knuckle 221 may be configured to provide a degree of freedom at the hinge region allowing the arm piece 220 to exhibit the desired range of motion. In one embodiment, the attachment point 221a is an orifice with a diameter greater than that of the pivot pin 219. In other embodiments, the attachment point 221a may be comprised of flexible material. One of ordinary skill in the art necessarily understands that the attachment point 221a can be any structure that provides the degree of freedom to allow the arm piece 220 to exhibit movement resulting in the desired toeing out motion of the plurality of blades 240.

Figure 15:
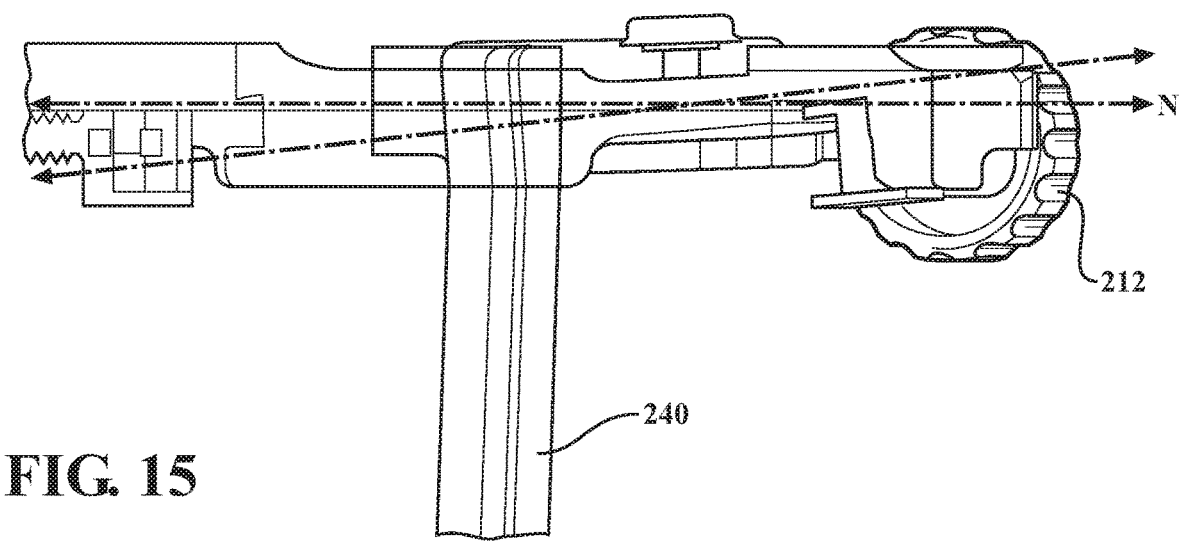
FIG. 15 is a side view illustrating the initial angle of the arm piece relative to the ring frame plane shown in FIG. 14.
Figure 16:
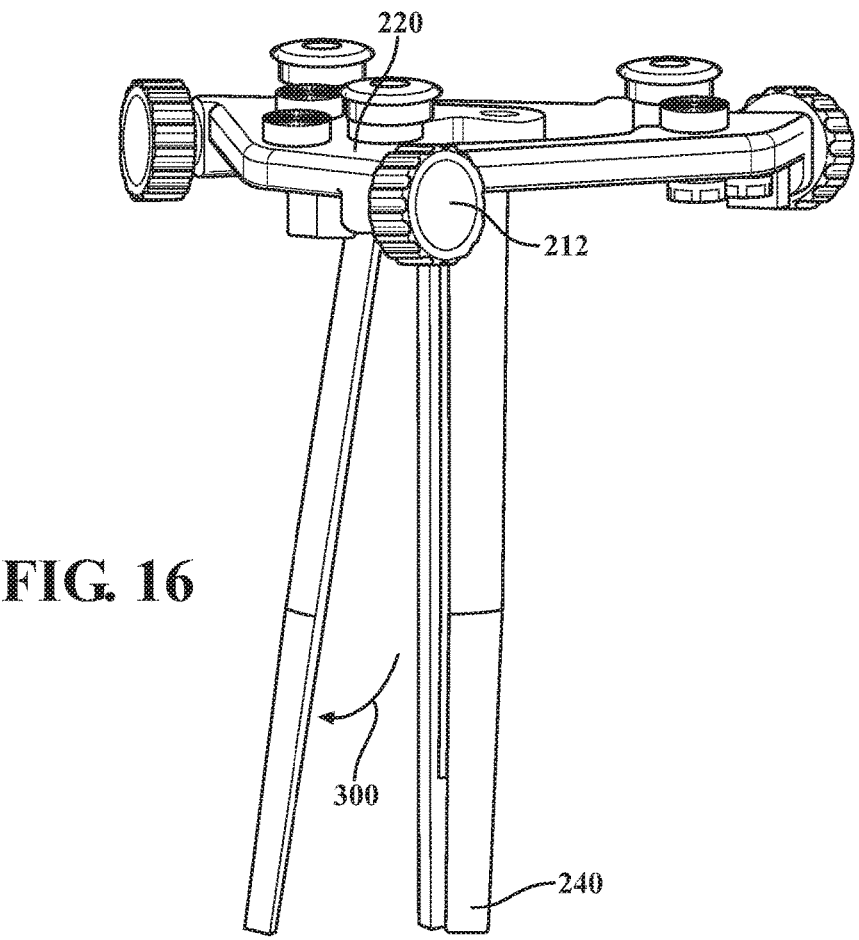
FIG. 16 is a perspective view illustrating one of the plurality of blades in an open and toed-out position.

In an embodiment as shown in FIG. 15, a normal plane N of the offset pivots generated by the cam 251 and cam follower 255 is angled relative to the top plane of the ring frame 230, represented by the dashed line, by between 1°-10°. Thus when the blades 240 are closed the transverse axis of the arm piece 220 is angled. As shown in FIG. 16, this angle causes the distal tip of the blade 240 to sweep in a downward direction 300 as the blade 240 opens. This downward sweep of the arm piece 220 compensates for the shortening of the effective length of the blade 240 due to the upward arc of the toeing blade 240 causing the tip of the opening blade 240 to remain in the same plane of the distal tips in the closed first position. This action prevents the opening blade 240 from lifting off the vertebral body as the blade 240 is toed out, which allows the surgeon to actuate the toeing out motion of the blade 240 without soft tissue slipping under the blade tip.

Figure 13:
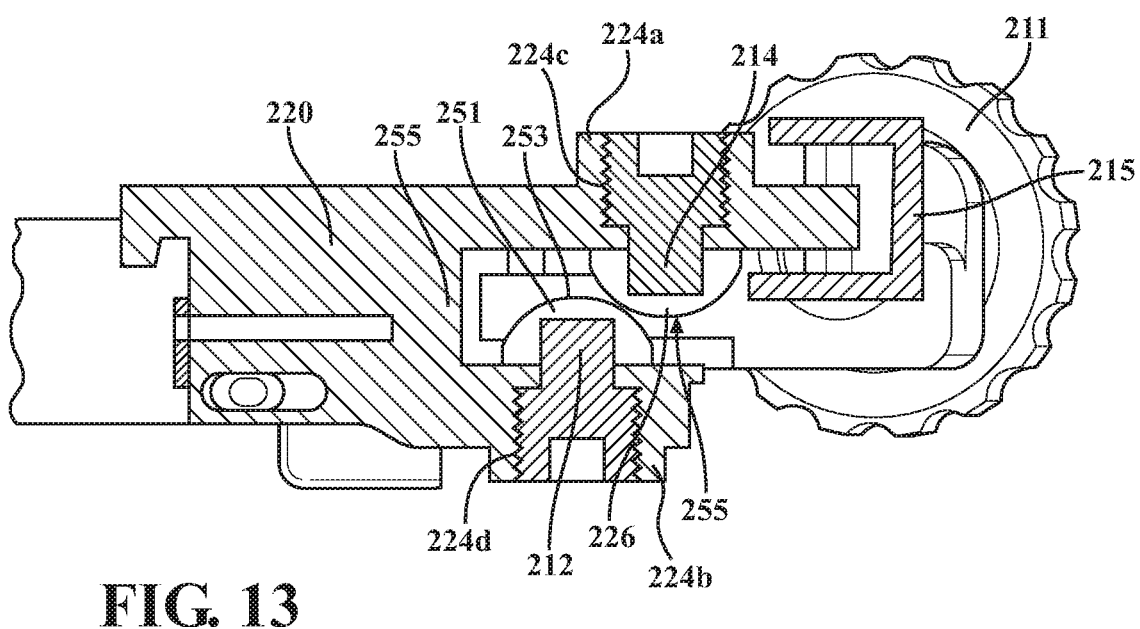
FIG. 13 is a cross-sectional view of the tissue retractor shown in FIG. 14 taken along line A-A, showing the actuating mechanism.
Figure 14:
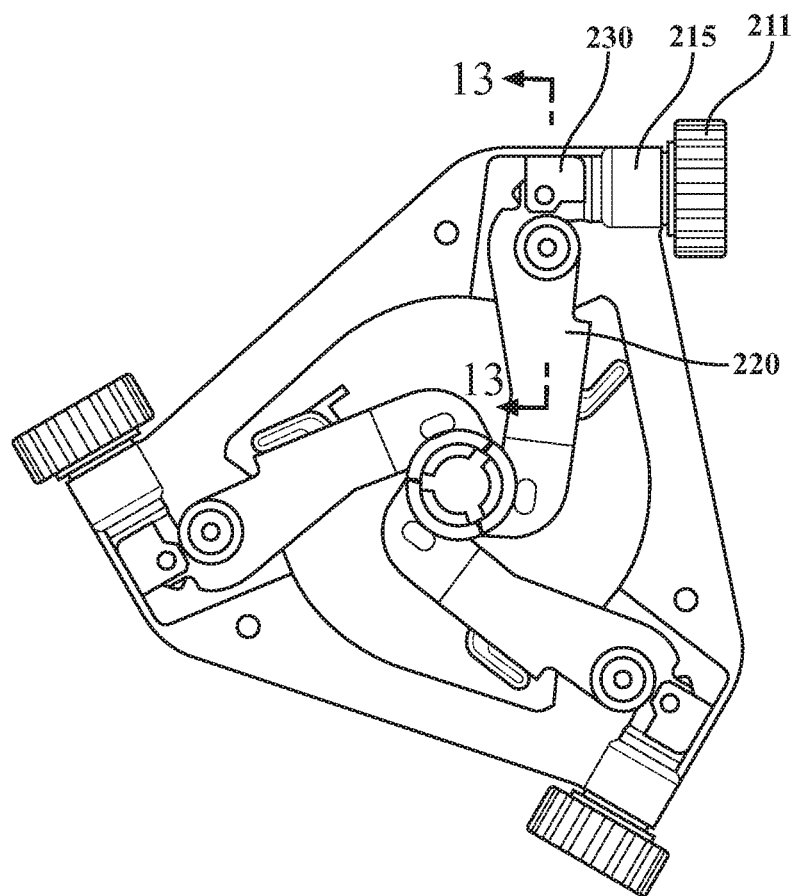
FIG. 14 is a top view of an example actuating mechanism.
Figure 18:
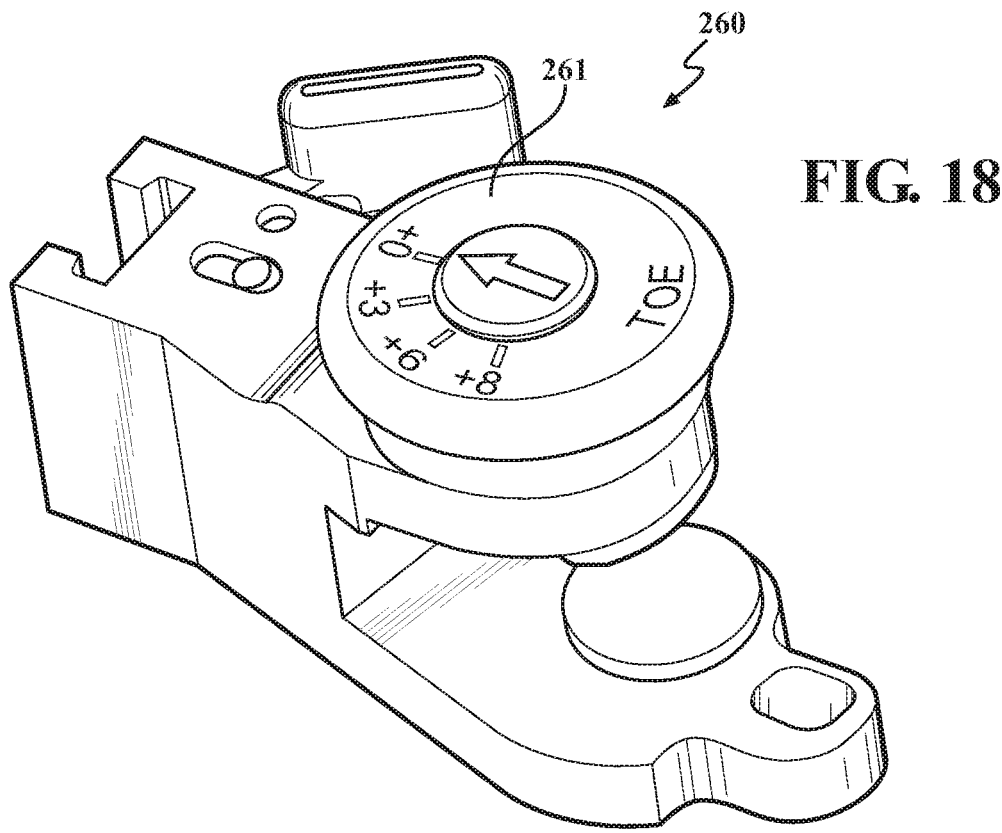
FIG. 18 is a perspective view of an assembled toe angle adjuster with an adjustment knob.
Figure 19:
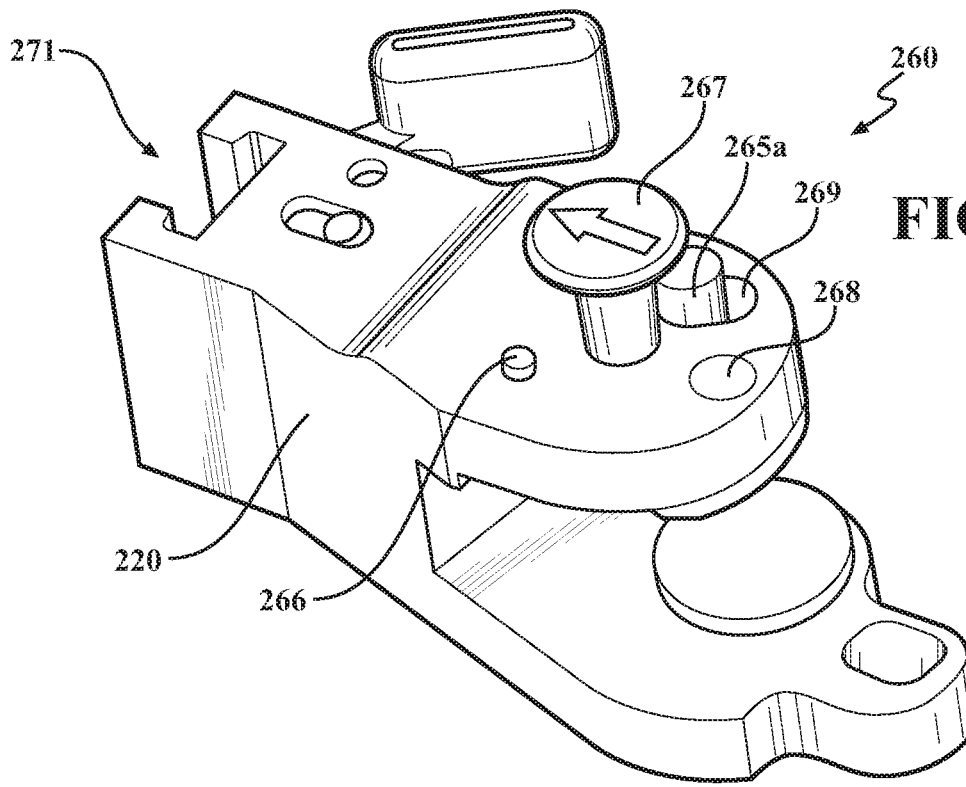
FIG. 19 is a perspective view of the assembled toe angle adjuster shown in FIG. 18 without the adjustment knob respectively.
Figure 20:
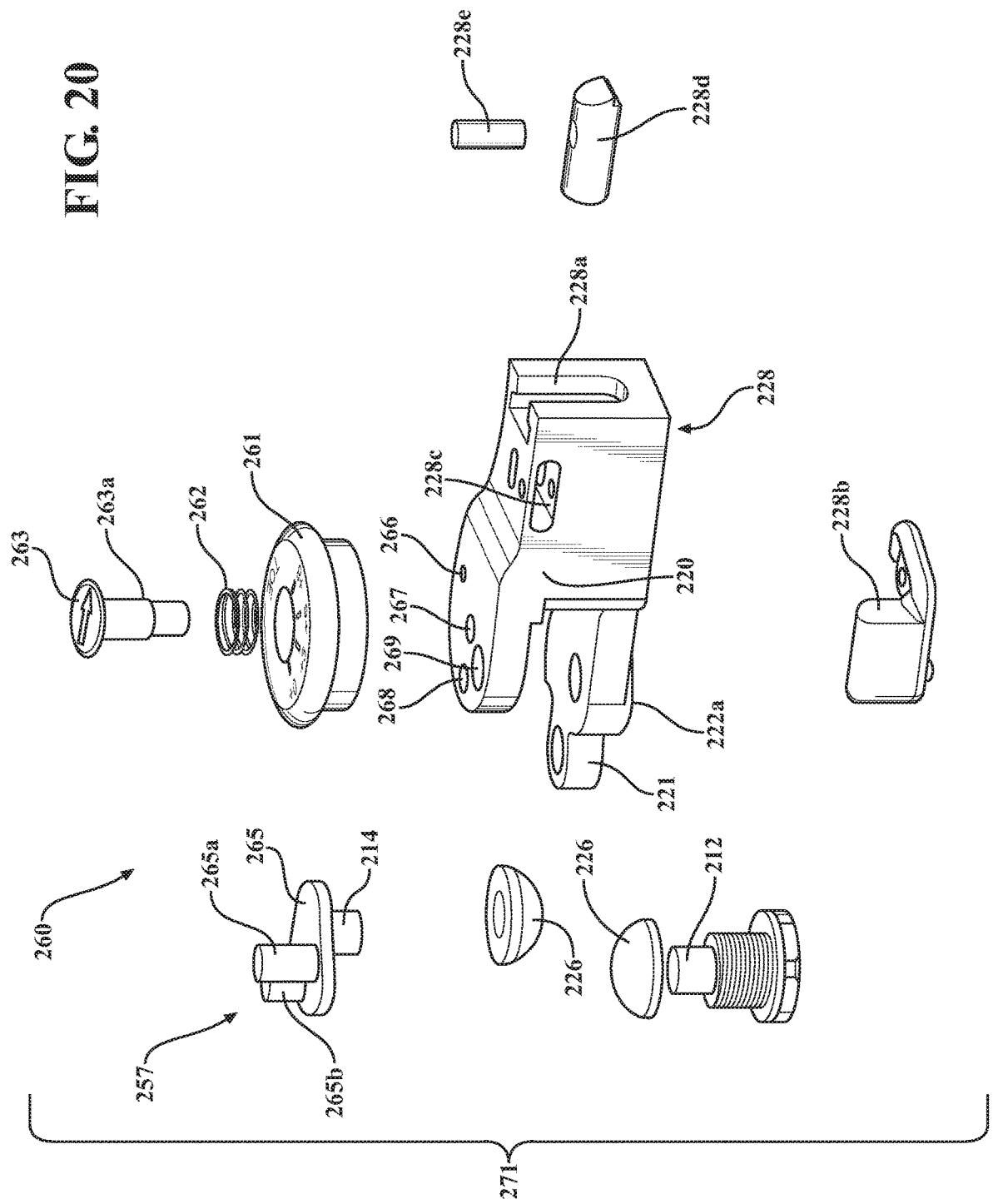
FIG. 20 is an exploded view of the example toe angle adjuster shown in FIG. 18.
Figure 21:
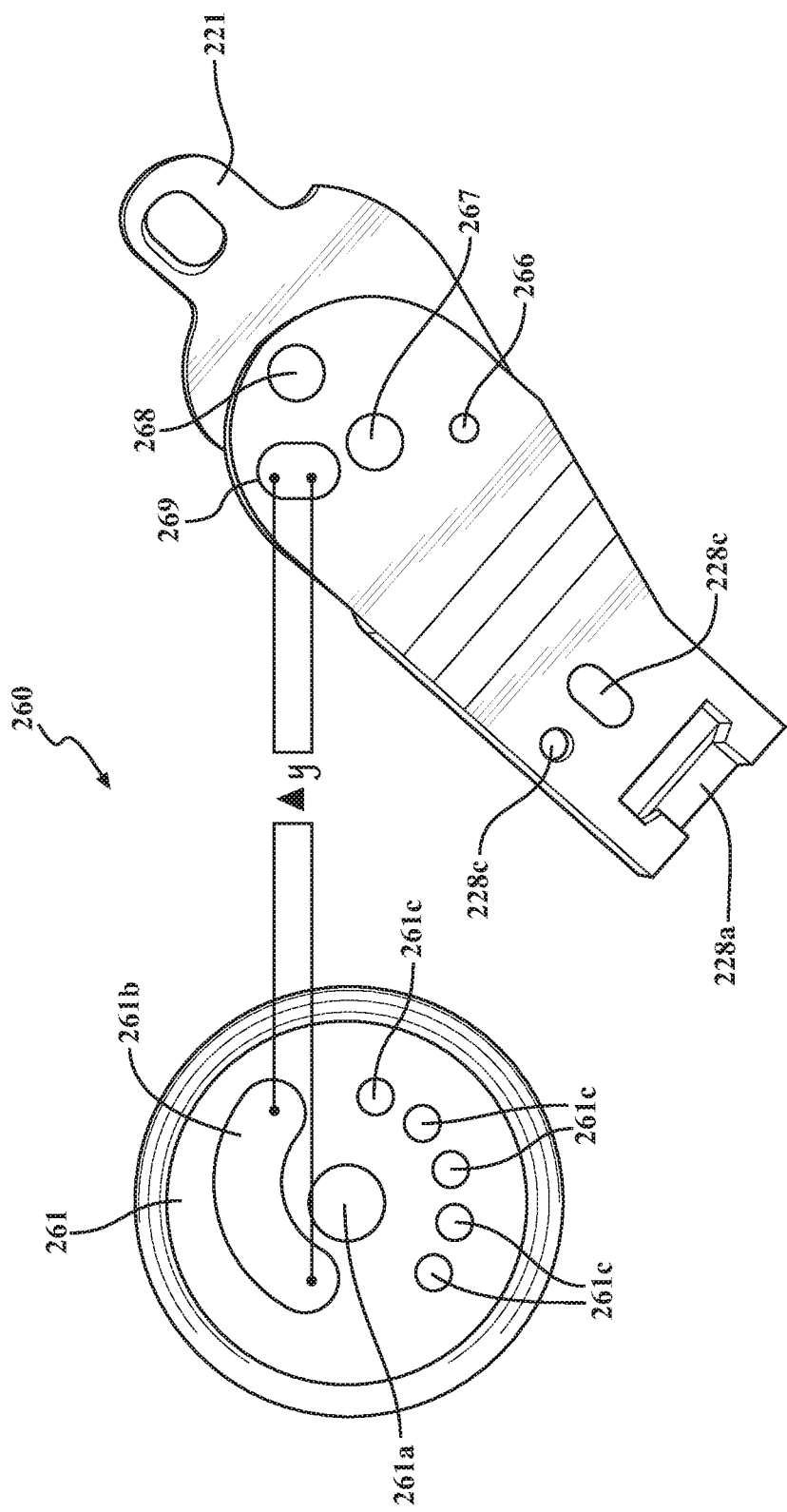
FIG. 21 is a bottom view of the adjustment knob and arm piece shown in FIG. 20.

As shown in FIGS. 18 and 19, the tissue retractor 200 may further include a toe angle adjuster 260. The toe angle adjuster 260 adjusts the initial tilt angle of the blade 240 in the first position. As shown in FIGS. 20 and 21, an embodiment of the toe angle adjuster 260 includes an adjustment knob 261, a bias spring 262, a set screw 263, a plate 265, an anchor stub 266, a set screw slot 267, an axle slot 268, and an adjustment track 269. In this exemplary embodiment, the plate 265 is disposed within the arm piece 220 such that the top surface of the plate 265 is in contact with the arm piece 220 and the second pivot post 214 opposes the first pivot post 212 in a similar position as the embodiment shown in FIGS. 13 and 14. When properly fit, an adjustment post 265a protrudes through adjustment track 269 and extends beyond the plane of the arm piece 220 surface. An axle 265b fits into axle slot 268 and provides the rotational axis for plate 265. The adjustment knob 261 is fit such that the set screw slot 267 is aligned with a central bore 261a, the protruding adjustment post 265a is housed within the displacement track 261b, and the anchor stub 266 is housed in a corresponding anchor notch 261c.

Adjustment knob 261 is configured to linearly displace the adjustment post 265a within the length of adjustment track 269. As shown in FIG. 21, the length of the adjustment track 269 corresponds to the displacement between the two ends of the displacement track 261b. In the example embodiment shown in FIG. 20, the second pivot post 224 and the cam follower 255 are disposed on the bottom surface of plate 265, thus displacement of the adjustment post 265a along the adjustment track 269 displaces the cam follower 255 with respect to the cam 251. The transferred motion causes rotational motion at the pivot points 251 and subsequent rotation of the arm piece 220 and toeing out of the blade 240 while in the first position. The depiction in FIG. 21 is merely for illustrative purposes and is not drawn to scale.

The anchor stub 266 fits into one of the plurality of anchor notches 261c to immobilize the adjustment knob 261 to a pre-calibrated position thus maintaining the desired initial toe angle. As illustrated in FIGS. 18 and 19 the adjustment knob 261 may have calibrated demarcations corresponding to each of the anchor notches 261c. The demarcations may be calibrated to provide initial toe angle adjustment from about 0° to about 45°, preferably from about 0° to about 15°, and most preferably from about 0° to about 10°. The demarcations can be incremented at about 0.5° increments to about 10° increments.

As shown in FIG. 20, the set screw 263 has a rim 263a preventing the screw from immobilizing the adjustment knob 261. Bias spring 262 is disposed about the set screw 263 and between the top surface of the adjustment knob 261 and the set screw head. The bias spring 262 provides sufficient normal force on the adjustment knob 261 such that the anchor notch 261c housing anchor stub 266 can maintain the selected initial toe angle. The bias spring 262 further allows the surgeon to pull up on the adjustment knob 261 to remove anchor stub 266 from anchor notch 261c and rotate the adjustment knob 261 to another position.

Now referring to FIGS. 22-26, a blade 470 having a blade mounting and adjustment mechanism 500 allowing for connection of the blade 470 to a lever 402 and adjustment of the depth of the blade 470 of the tissue retractor 400 is provided.

The blade 470 may be used with a retractor 400 having a housing 406 adapted to connect with the adjustment mechanism 500 of the blade 470. It should be appreciated that any retractor, including the retractors disclosed herein may be adapted to include the housing 406. The adjustment mechanism 500 includes a threaded portion 466 formed on the blade 470. The adjustment mechanism 500 further includes an adjustment screw 480, at least a portion of the adjustment screw being threaded. The adjustment screw 480 connects the blade 470 to the lever 402 by means of the housing 406. The threaded portion 466 of the blade 470 is mechanically coupled to the threaded portion of the adjustment screw 480 wherein rotation of the adjustment screw 480 displaces the blade 470 in a vertical arrangement thereby allowing for adjustment of the depth of the blade 470.

In this embodiment, the adjustment mechanism 500 is mounted to the blade 470 of the retractor. Furthermore, a spring loaded locking lever 408 is connected to the threaded portion of the adjustment screw 480, the locking lever 408 movable with the adjustment screw 480 during depth adjustment.

Accordingly, the blades 470 may be adjusted in depth so as to eliminate the use of shims used to increase the overall length of a typical blade. Further, the depth adjustment mechanism is disposed on the blade 470 itself and integrates with the blade 470 itself thereby minimizing the size of the retractor so the surgeon has the maximum amount of visualization when taking photos or performing a procedure.

An important factor in blade 470 height adjustment is the size of the mount. As used herein, the mount refers to the structure for supporting the blade 470 to the retractor. The adjustment mechanism 500 allows for both adjustment and attachment of the blade 470 to the lever 402, while maintaining a smaller physical dimension relative to currently known mounts. Minimizing the size of the mount provides the surgeon with a greater field of view and camera angle when taking photos or performing a procedure. Having a blade 470 with an adjustment mechanism described herein minimizes the size of the blade mount by integrating blade locking and height adjustment features in one package.

Once locked, the rotating adjustment screw 480 allows for continuous blade height adjustment. FIGS. 22-29 illustrate several embodiments of a retractor 400 having an adjustment mechanism 500. Although the disclosed embodiments illustrate a retractor 400 having two handles 410 squeezable to facilitate expansion of the blades 470, other embodiments such as the ring embodiment may also include the adjustment mechanism 500 described herein.

The retractor assembly 400 includes at least one lever 402 having a distal end 404. The distal end 404 is adapted to connect to the blade 470. The levers 402 are generally elongated and are adapted to connect with the blades 460 at a housing 406. The blades 470 connect and lock to the distal end 404 of the lever 402 by means of the locking lever 408. The levers 402 further include handles 410 with locking mechanisms 412, 414. The retractor 400 further includes mounting members 416, 418 adapted to mount to at least one surgical table arm 490. In the present embodiment, the retractor 400 is shown having a posterior arm 420 providing for connection to a third posterior blade. The posterior blade arm 420 also includes the adjustment mechanism 500.

The blade 470 includes a distal end 471 and a corresponding proximal end 473. A curved arm 474 extends outwardly from the proximal end of the blade 470 and is generally orthogonal to the axial length of the blade 470. The curved arm 474 is adapted to hold the adjustment mechanism 500 and to place the blades 470 in a position to form a generally cylindrical surgical corridor when pressed together in a first position as shown in FIG. 22. The adjustment mechanism 500 is partially shown in FIG. 24 and fully illustrated in FIGS. 28 and 29. The adjustment mechanism 500 includes a partially open bore 464 at the distal end of the arm 474. The bore 464 includes a threaded portion 466 along at least a portion of the interior surface of the bore 464. The adjustment portion 500 further includes an outer surface 462 adapted to form a generally smooth outer surface with the lever 402. Indentations 472 are provided to connect with the distal end of the lever 402.

The adjustment mechanism 500 includes the adjustment screw 480. The adjustment screw 480 includes a threaded portion 482 and a head 484. The threaded portion 482 covers at least a portion of the outer surface 481 of the adjustment screw 480. The threaded portion 482 is adapted to connect with the threaded portion 466 of the bore 464. An upper lip 468 may be further provided at an upper portion of the bore 464. The lip 468 may be slightly crimped to prevent the adjustment screw from dislodging. Alternatively or in addition to, a harness 486 is provided to prevent dislodgment of the adjustment screw 480 during adjustment. The harness 486 includes an aperture to accept the set screw 488. The set screw 488 is adapted to secure to the aperture 489 of the arm 474 of the blade 470. The harness 486 includes a U-shaped portion 491 adapted to connect to the adjustment screw 480.

The distal portion of the lever 402 is adapted to hold the locking lever 408. The locking lever 408 includes a notch 492 adapted to connect to the threaded portion 482 of the adjustment screw 480. The locking lever 408 further includes an aperture 493 adapted to connect to a pin 434. The pin 434 allows for the locking lever 408 to pivot and thus release from the adjustment screw 480. The locking lever 408 includes a handle portion 495 allowing the user to rotate the locking lever 408 about the pivot pin 434. Rotation of the locking lever 408 results in unlocking of the adjustment mechanism 500 and thus release of the blade 470.

The adjustment mechanism 500 is mounted to the blade 470 and directly locks to the locking lever 408. Once the locking lever 408 is released, the entire blade 470 is also accordingly released and thus can be removed. The locking lever 408 is mounted to the lever 402 by the pivot pin 434 that allows the top of the locking lever 408 to act against a spring and thus swing open. The threaded portion 482 of the adjustment screw 480 slides down a ramped portion 497 on the locking lever 408 causing the lever 408 to swing open as the blade 470 is inserted into the lever 402. The threaded portion 482 of the adjustment screw 480 has defined edges that create a cylindrical shape which engages the notch 492 of the locking lever 408. The notch 492 includes a plurality of generally planar surfaces arranged to securely accept the threaded portion 482 of the adjustment screw. The threaded portion 482 of the adjustment screw 480 is captured by the indentation 492 and held in a closed position by a spring that acts behind the locking lever 408 and is contained within the lever 402. When the locking lever 408 is closed around the threaded portion 482 of the adjustment screw 480, the adjustment screw 480 is free to rotate and thus adjust the height or depth of the blade 470.

Depth adjustment of the blade is accomplished by rotation adjustment screw 480. Specifically, rotation head 484 actuates rotation of the adjustment screw 480. In the present embodiment, a wrench is used to turn the adjustment screw at the head 484. In other embodiments, a nut or other handle connected to the adjustment screw may be utilized to rotate the adjustment screw 480.

The threaded portion 482 of the adjustment screw 480 mates with a threaded portion 466 of the bore 464. As the adjustment screw 480 is rotated, the blade 470 can be raised or lowered as the threaded portion 482 of the adjustment screw 480 moves up and down in the bore 464. The threaded portion 482 of the adjustment screw 480 mates with the threaded portion 466 of the bore 464. Rotation of the adjustment screw 480 results in a downward or upward motion of the blade 470. The arm 474 of the blade 470 accordingly is displaced as the adjustment screw is rotated.

Figure 25:
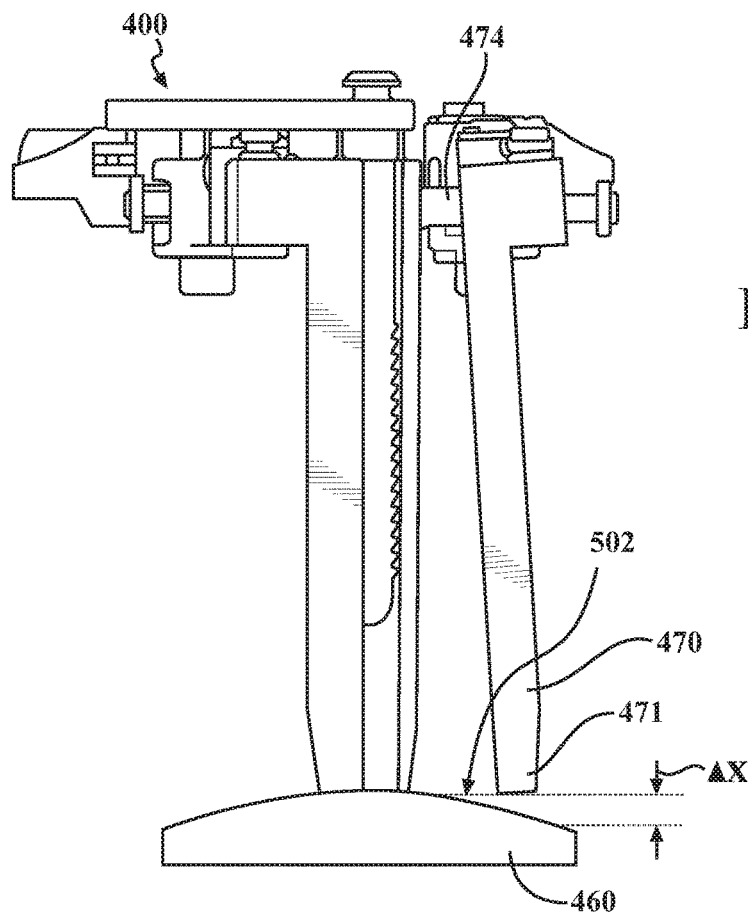
FIG. 25 is a side view of the retractor shown in FIG. 22 before depth adjustment.
Figure 26:
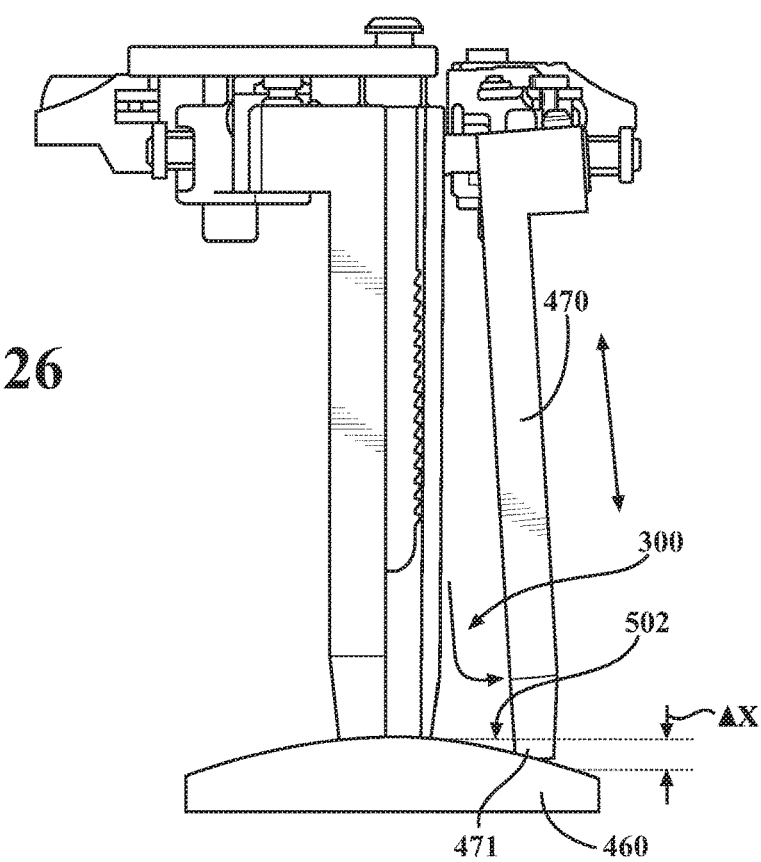
FIG. 26 is a side view of the retractor shown in FIG. 22 after depth adjustment.

FIGS. 25 and 26 illustrate rotation and height adjustment of the blade 470. FIG. 25 illustrates the retractor 400 having the blade 470 before any adjustment. A bone surface 460 is provided at the distal end 471 of the blade 470. As illustrated in FIG. 25, before a height adjustment of the blade 470, the distal end 471 is spaced apart from a bone surface 460. The gap ΔX between the bone surface 460 and the distal end 471 of the blade 470 may result in soft tissue encroaching into the surgical site 502. In the present embodiment, ΔX ranges between 5-6 millimeters. However, in other embodiments, ΔX may range up to 10 millimeters. FIG. 26 illustrates the blade 470 after it has been adjusted allowing the distal end 471 of the blade 470 to contact the bone 460. This adjustment thereby prevents encroachment of soft tissue into the surgical site 502.

In the present embodiment, a third posterior blade arm 420 is also provided. The arm 420 may also be adjusted in a forward and rearward direction by means of the adjustment screw 442. Rotation of the adjustment screw 442 results in forward and rearward motion of the arm 420. In the present embodiment, the adjustment screw 442 is adjusted with a hexagonal wrench. In other embodiments a handle or other rotation nut may be provided for adjustment. The blade connected to the posterior blade arm 420 is typically the blade that is anchored to the vertebrae or the annulus of the disc/the other wall of the disc itself.

Figure 27:
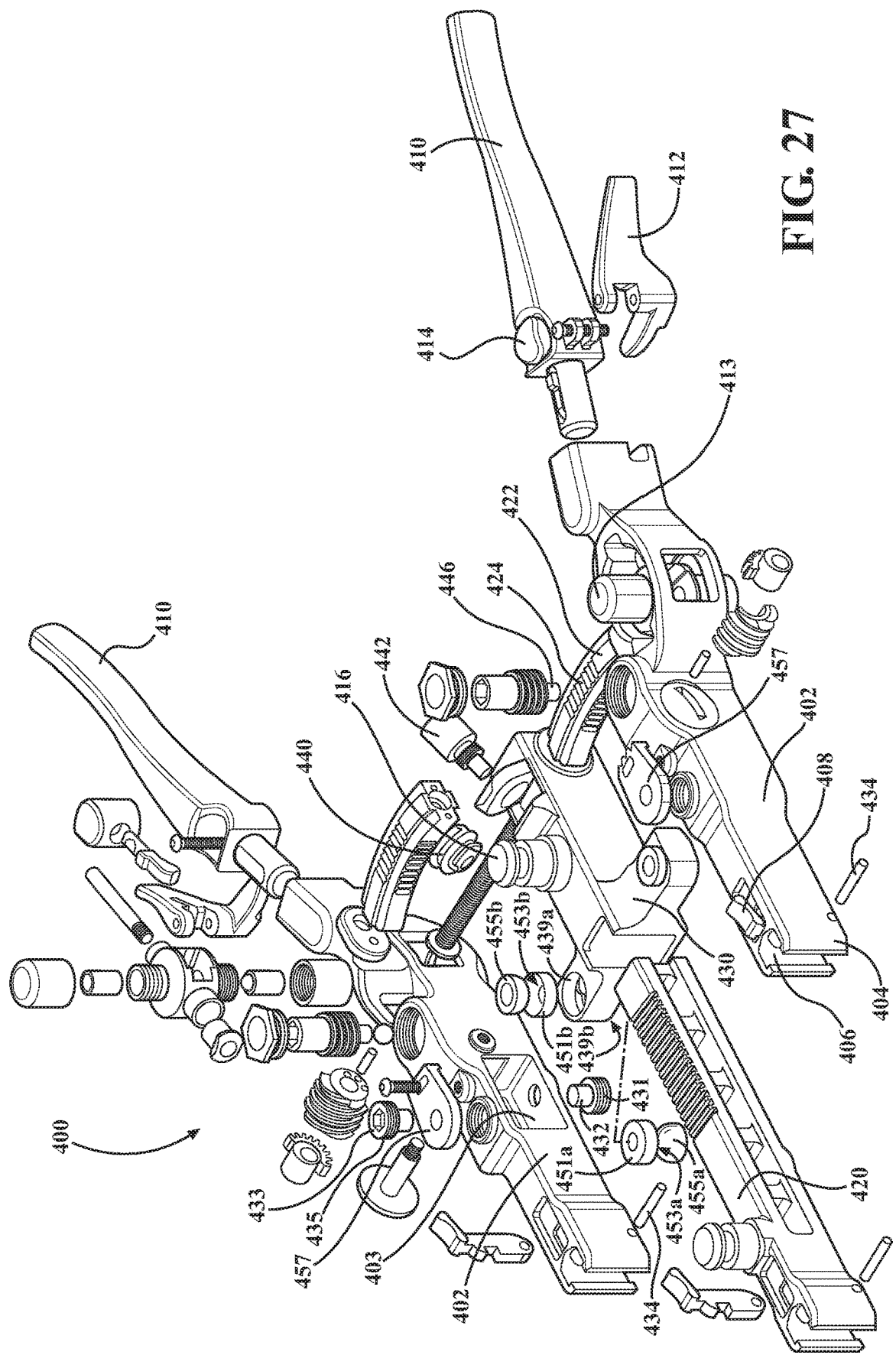
FIG. 27 is an exploded perspective view of the tissue retractor shown in FIG. 22.
Figure 28:
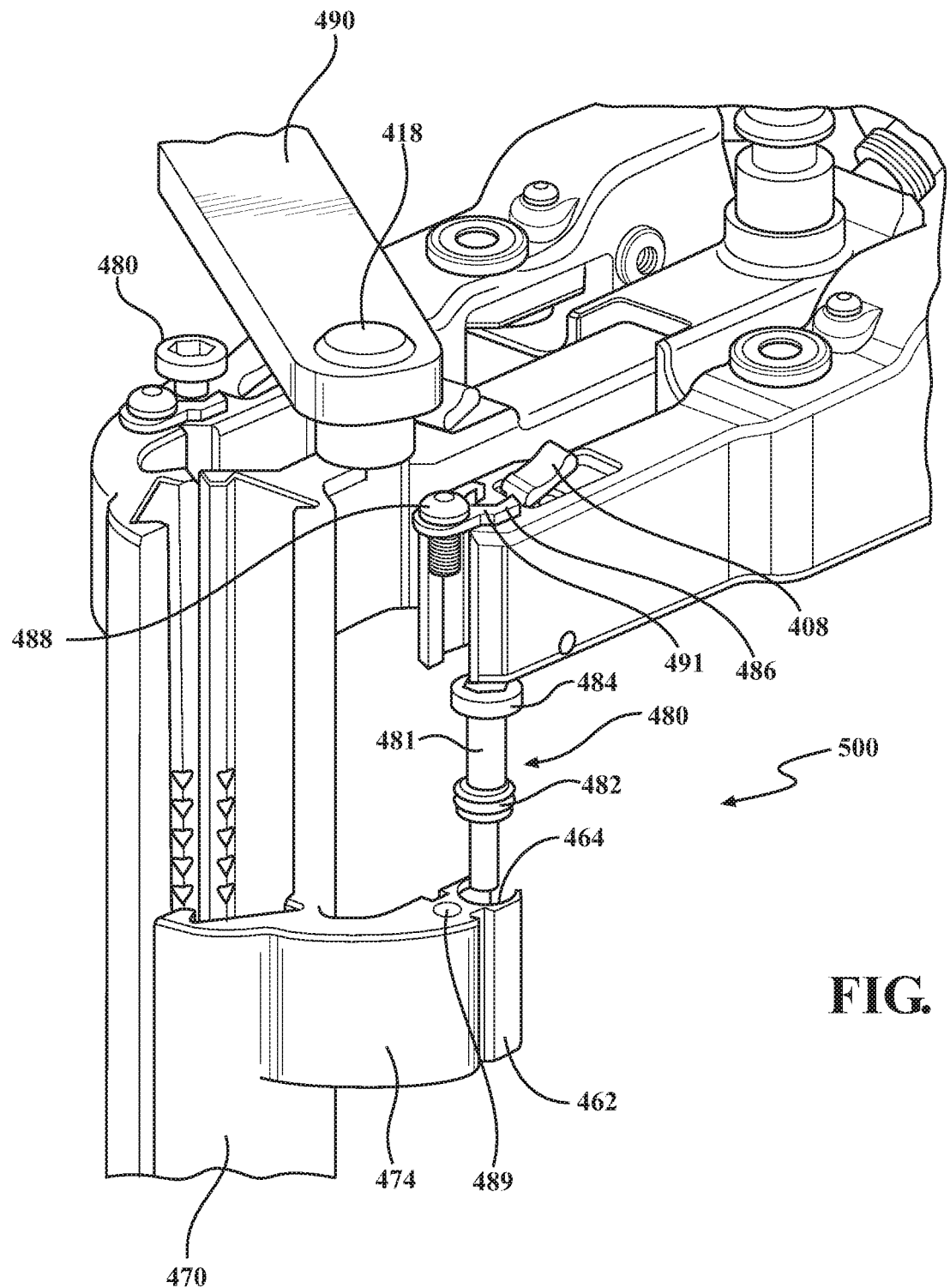
FIG. 28 is a partially exploded perspective view of the retractor and the blade shown in FIG. 22.
Figure 29:
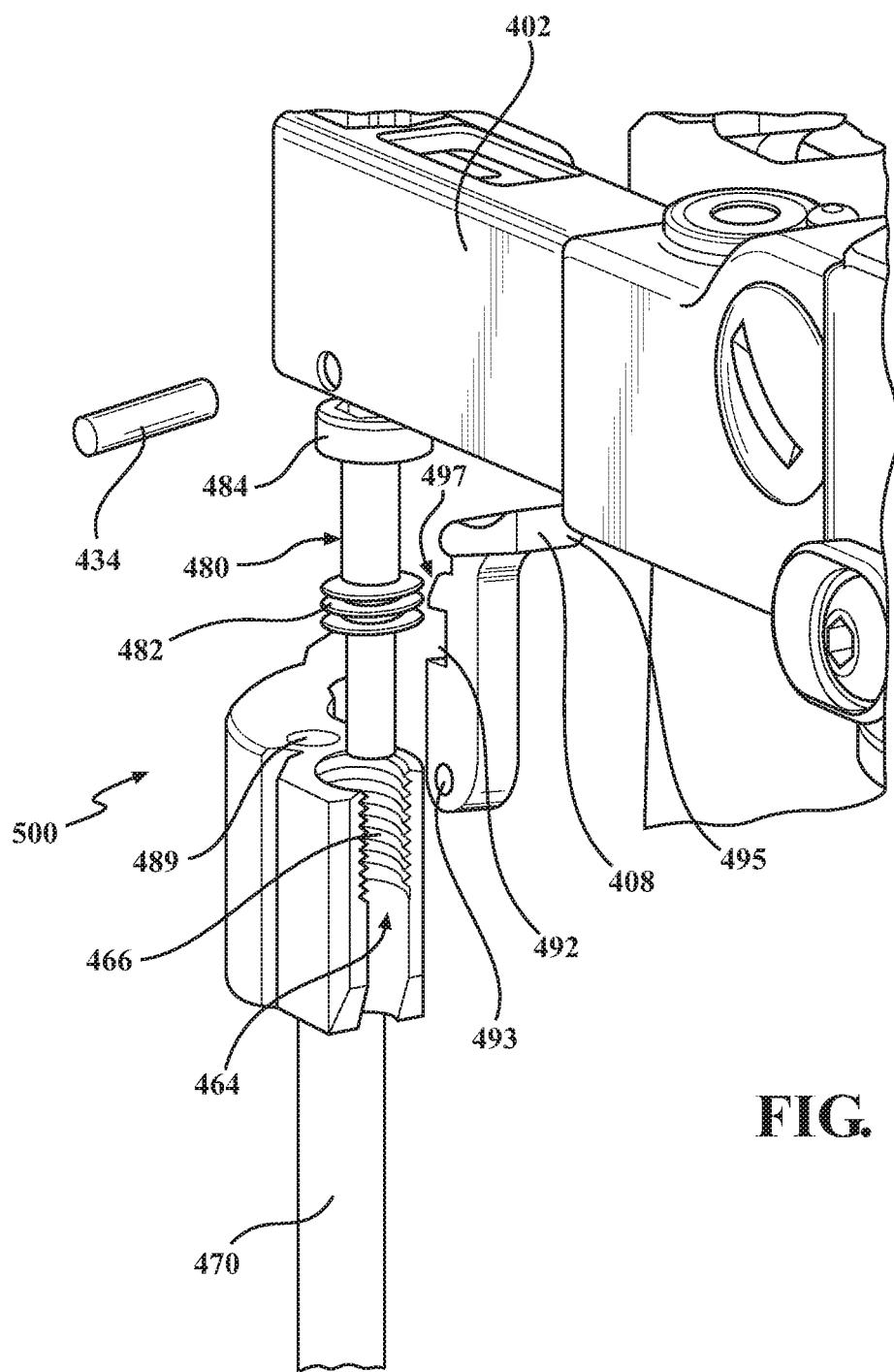
FIG. 29 is a front view of the retractor shown in FIG. 28.

The retractor 400 may be further configured to automatically perform a toe-out motion when the handles 410 are squeezed together. With reference now to FIG. 27, each lever 402 includes at least one cam follower 455 mounted thereto. In the present embodiment, the lever 402 includes two cam followers 455a, 455b. The cam follower 455a is mounted to the arm 402 within the aperture 403. The cam follower 455a is mounted by means of a post 432 connected to the lever 402. The post 433 includes a threaded portion 431 adapted to secure to a lower portion of the lever 402. The post 432 extends through the lower portion of the lever 402 and connects directly with the cam follower 455a.

The cam follower 455b connects to the lever 402 by means of a plate 457. The plate 457 is mounted to the arm 402 by a post 433. The post 433 includes a threaded portion 435 adapted to secure to an upper portion of the lever 402. The post 433 extends through the upper portion of the lever 402 and connects directly with the plate 457. The plate 457 includes a post (not shown) extending orthogonally from a lower surface 459. The post is adapted to connect with and secure the cam follower 455b to the plate 457.

Corresponding cams 451a, 451b include curved inner cam surfaces 453a, 453b adapted to operatively connect with respective cam followers 455a, 455b. The cams 451a, 451b are fixedly connected to the flange 430 within the apertures 439a, 439b. In this embodiment, the cams 451a, 451b and corresponding apertures 439a, 439b are offset. The cam followers 455a, 455b rest within the respective cams 451a, 451b and are free to pivot and rotate within the cams 451a, 451b when the handles 460 are squeezed together. When the handles 460 are squeezed together, the lever 402 is free to pivot about the cams 451a, 451b resulting in independent pivot action of the blade 470 (mounted to the lever 402) to cause the distal end of the blade to project out radially with respect to the proximal end of the blade.

In this embodiment, the cam followers 455a, 455b are generally spherical elements having a rounded outer surface. Correspondingly, the cam surfaces 453a, 453b have a concave generally spherical surface. It should be appreciated that other geometries of both the cam followers 455a, 455b and the cam surfaces 453a, 453b may include varying geometry to accommodate the toe-out requirements of the blade 470.

The blades 470 in a first position form a cylindrical surgical corridor, which may be used with other medical instruments such as, for example, a dilator. In the first position, the blades 470 may be inserted over the dilator. As the levers 402 are actuated, the levers 402 will simultaneously be urged together and rotate in a multi-plane motion causing the top and bottom sides of the jaws to follow separate arc lengths providing simultaneous opening and providing toeing action to the plurality of blades 470. Expansion of the plurality of blades 470 will result in a toe angle in a second position (partially open view shown in FIGS. 25 and 26). The offset length between the cams 451 determines the opening angle and toe angle. The amount of tilt generated is a sinusoidal relation to the opening angle which increases in gain as the opening angle increases.

The blades 470 are attached to the distal ends of the levers 402. In other embodiments, only one blade 470. The blades 470 may be attached by welding or may be cast as a continuous extension from the lever. In other embodiments not shown, the blades 470 are detachable and have tangs disposed at the proximal end of each blade 470. The blade tangs fit into corresponding recess disposed at the distal end of each lever.

The curved portion 422 is adapted to be inserted through the lever 402. It is inserted through an aperture with a larger dimension thus allowing the curved member 422 tolerance within the aperture during toe-out. The radius of curvature of the curved arm 422 corresponds to the radius of the pivot of the lever 402. The release mechanism 412 connected to the handle 410 communicates with the curved portion 422. As the release member 412 is actuated, the curved portion is disengaged. Actuation of the release mechanism 412 results in release of the locking member 413.

The locking member 413 connects with the curved portion 422 and the notch portions 424 of the curved portion 422. In an alternative embodiment, the locking portion 413 is adapted to have a pin or other connection portion connecting to a notch portion on the curved member. Such an adjustment lock will allow the surgeon to slightly advance back if the retractor was open too far. Without the locking portion 413, the forces on the blades 470 would force the retractor mechanism shut, or slam the retractor shut. The locking mechanism with slight adjustment would allow for the surgeon to gradually close the retractor for slight inward adjustment. The locking member 413 may include a twisting device so that when you squeeze the release lever the handle can be moved inward without the retractor slamming shut.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

The invention claimed is:

1. A tissue retractor comprising:
a frame for supporting a first blade and a second blade the frame configured to displace the first blade away from the second blade so as to define a surgical corridor, the frame having a housing with a first longitudinal axis, the housing receiving a portion of the first blade;
a pivoting mechanism configured to adjust an angle of the first blade with respect to the frame so as to widen a distal end of the surgical corridor;
an adjustment mechanism received by the housing and operating independently of the pivoting mechanism, the adjustment mechanism having a threaded adjustment screw adapted to rotate within a threaded bore of the first blade, the threaded bore having a second longitudinal axis that is parallel to the first longitudinal axis and parallel to and spaced apart from a longitudinal length of the first blade;
wherein rotation of the adjustment screw causes the first blade to move in a direction parallel to the longitudinal axis of the threaded bore; and
wherein said movement is constrained to the second longitudinal axis thereby allowing for adjustment of a depth of the first blade with respect to the frame without adjusting the angle of the first blade, accordingly, the first blade may be raised or lowered while angled.

2. The tissue retractor of claim 1, wherein the first blade includes a curved arm generally orthogonal to an elongated axis of the blade, the curved arm adapted to hold the adjustment mechanism.

3. The tissue retractor of claim 2, wherein the blade includes a threaded bore adapted to connect with the adjustment screw of the adjustment mechanism.

4. The tissue retractor of claim 2, wherein the adjustment mechanism is adapted to connect with a housing on the tissue retractor.

5. A tissue retractor comprising:
a first blade and a second blade coupled together so as to define a surgical corridor;
a pair of levers mechanically connected to the first blade and the second blade so as to widen the surgical corridor, each of the pair of levers includes a housing with a longitudinal axis, a cam follower, and a cam mechanically connected to each other so as to pivot the first and second blade so as to widen a distal end of the surgical corridor;
a blade adjustment mechanism configured to adjust a depth of the first blade;
wherein the first blade includes a threaded bore and the blade adjustment mechanism is mounted thereto, the threaded bore having a longitudinal axis that is parallel to the longitudinal axis of one housing and spaced apart from and parallel to a longitudinal length of the first blade, the adjustment mechanism having an adjustment screw, at least a portion of the adjustment screw being threaded, the adjustment screw configured to engage the threaded bore and connect the first blade to the housing of the lever;
wherein rotation of the adjustment screw causes the first blade to move vertically constrained to the longitudinal axis of the threaded bore thereby allowing for adjustment of the depth of the first blade without adjusting an angle of the second blade.

6. The tissue retractor of claim 5, wherein a spring loaded lock is connected to the threaded portion of the adjustment screw, the spring-loaded lock movable with the adjustment screw during depth adjustment.

7. The tissue retractor of claim 5, wherein the adjustment mechanism is connected to an extended arm portion of the first blade.

8. The tissue retractor of claim 5, wherein ratcheting is incorporated to provide sensory feedback to the user regarding the amount of movement of the first blade.

9. The tissue retractor of claim 5, wherein the first blade has a maximum distal displacement of up to 10 millimeters.

10. A tissue retractor comprising:
a frame for supporting multiple retractor blades and configured to displace the blades so as to define a surgical corridor, the frame having a housing for receiving a first retractor blade;
a pivoting mechanism configured to adjust an angle of the multiple retractor blades with respect to the frame so as to widen a distal end of the surgical corridor;
the first retractor blade having a portion of a proximal end configured to be received by the housing of the frame, the proximal end having threaded bore with a longitudinal axis parallel to a longitudinal axis of the first retractor blade and parallel to a longitudinal axis of the housing;
an adjustment mechanism functionally connecting the housing and the threaded bore;
wherein rotating the adjustment mechanism causes the portion of the proximal end to move along the longitudinal axis of the housing thereby longitudinally displacing the first retractor blade along the longitudinal axis of the first retractor blade.

11. The tissue retractor of claim 10, wherein the portion of the proximal end of the first blade comprises a curved arm generally orthogonal to the longitudinal axis of the blade.

12. The tissue retractor of claim 10, wherein a spring loaded lock is connected to the adjustment mechanism, the spring-loaded lock movable with the adjustment mechanism during longitudinal displacement of the first retractor blade.

13. The tissue retractor of claim 10, wherein the adjustment mechanism is connected to an extended arm portion of the first blade.

14. The tissue retractor of claim 10, wherein ratcheting is incorporated to provide sensory feedback to a user regarding the amount of movement of the first blade.

15. The tissue retractor of claim 10, wherein the first blade has a maximum longitudinal displacement of up to 10 millimeters.

16. The tissue retractor of claim 10, wherein the threaded bore is open along one side.

17. The tissue retractor of claim 10, wherein the adjustment mechanism comprises a threaded portion configured to engage the threaded bore and a head configured to abut an edge of the housing to maintain a longitudinal orientation of the adjustment mechanism relative to the frame.

18. The tissue retractor of claim 10, further comprising a harness configured to prevent dislodgment of the adjustment mechanism during adjustment.

19. The tissue retractor of claim 10, wherein the adjustment mechanism and the pivoting mechanism operate independently of each other.

* * * * *